(12) United States Patent
Page et al.

(10) Patent No.: US 8,584,535 B2
(45) Date of Patent: Nov. 19, 2013

(54) LIQUID TO LIQUID BIOLOGICAL PARTICLE CONCENTRATOR WITH DISPOSABLE FLUID PATH

(75) Inventors: Andrew Edward Page, Smithton, MO (US); Zachary A. Packingham, Drexel, MO (US); David Scott Alburty, Drexel, MO (US); Alec D. Adolphson, Raymore, MO (US)

(73) Assignee: Innova Prep LLC, Drexel, MO (US)

( * ) Notice: Subject to any disclaimer, the term of this patent is extended or adjusted under 35 U.S.C. 154(b) by 326 days.

(21) Appl. No.: 12/882,188

(22) Filed: Sep. 14, 2010

(65) Prior Publication Data

US 2011/0061474 A1 Mar. 17, 2011

Related U.S. Application Data

(60) Provisional application No. 61/276,737, filed on Sep. 17, 2009.

(51) Int. Cl.
*G01N 1/22* (2006.01)
*G01N 1/10* (2006.01)
*G01N 1/14* (2006.01)
*C02F 1/44* (2006.01)

(52) U.S. Cl.
USPC ............... 73/863.23; 73/863.71; 73/864.01; 73/864.11; 73/864.14; 210/321.65; 210/321.87; 210/650

(58) Field of Classification Search
USPC .......................... 73/863.23, 864.11
See application file for complete search history.

(56) References Cited

U.S. PATENT DOCUMENTS

| | | | |
|---|---|---|---|
| 4,401,646 A * | 8/1983 | Rhodes et al. ............... | 424/1.49 |
| 6,589,314 B1 * | 7/2003 | Page et al. .................... | 95/32 |
| 6,692,968 B2 * | 2/2004 | Bell et al. ..................... | 436/63 |
| 6,857,436 B2 * | 2/2005 | Labib et al. ................... | 134/22.1 |
| 7,799,279 B2 * | 9/2010 | Fulton et al. .................. | 422/425 |
| 7,998,731 B2 * | 8/2011 | Daitch et al. ................. | 435/309.1 |
| 8,110,112 B2 * | 2/2012 | Alburty et al. ................ | 210/650 |
| 8,158,064 B2 * | 4/2012 | Fulton et al. .................. | 422/110 |
| 8,334,097 B2 * | 12/2012 | Lloyd et al. ................... | 435/6.1 |
| 8,336,403 B2 * | 12/2012 | Tajima ......................... | 73/864.11 |
| 2002/0182114 A1 * | 12/2002 | Ingenhoven et al. ........... | 422/99 |
| 2005/0163689 A1 * | 7/2005 | Akerman et al. .............. | 423/177 |
| 2007/0151924 A1 * | 7/2007 | Mir et al. ...................... | 210/637 |
| 2008/0257073 A1 * | 10/2008 | Tajima ......................... | 73/864.11 |
| 2009/0019955 A1 * | 1/2009 | Mao et al. ..................... | 73/864.11 |
| 2011/0067505 A1 * | 3/2011 | Page et al. .................... | 73/863.23 |
| 2011/0197685 A1 * | 8/2011 | Alburty et al. ............... | 73/863.23 |

* cited by examiner

*Primary Examiner* — Leonard Chang
*Assistant Examiner* — Natalie Huls
(74) *Attorney, Agent, or Firm* — Moazzam & Associates, LLC

(57) ABSTRACT

Highly efficient and rapid filtration-based concentration devices, systems and methods are disclosed with sample fluidic lines and a filter packaged in a disposable tip which concentrate biological particles that are suspended in liquid from a dilute feed suspension. A sample concentrate or retentate suspension is retained while eliminating the separated fluid in a separate flow stream. The concentrate is then dispensed from the disposable tip in a set volume of elution fluid. Suspended biological particles include such materials as proteins/toxins, viruses, DNA, and/or bacteria in the size range of approximately 0.001 micron to 20 microns diameter. Concentration of these particles is advantageous for detection of target particles in a dilute suspension, because concentrating them into a small volume makes them easier to detect. All conduits by which the disposable tip attaches to the instrument are combined into a single connection point on the upper end of the tip.

11 Claims, 18 Drawing Sheets

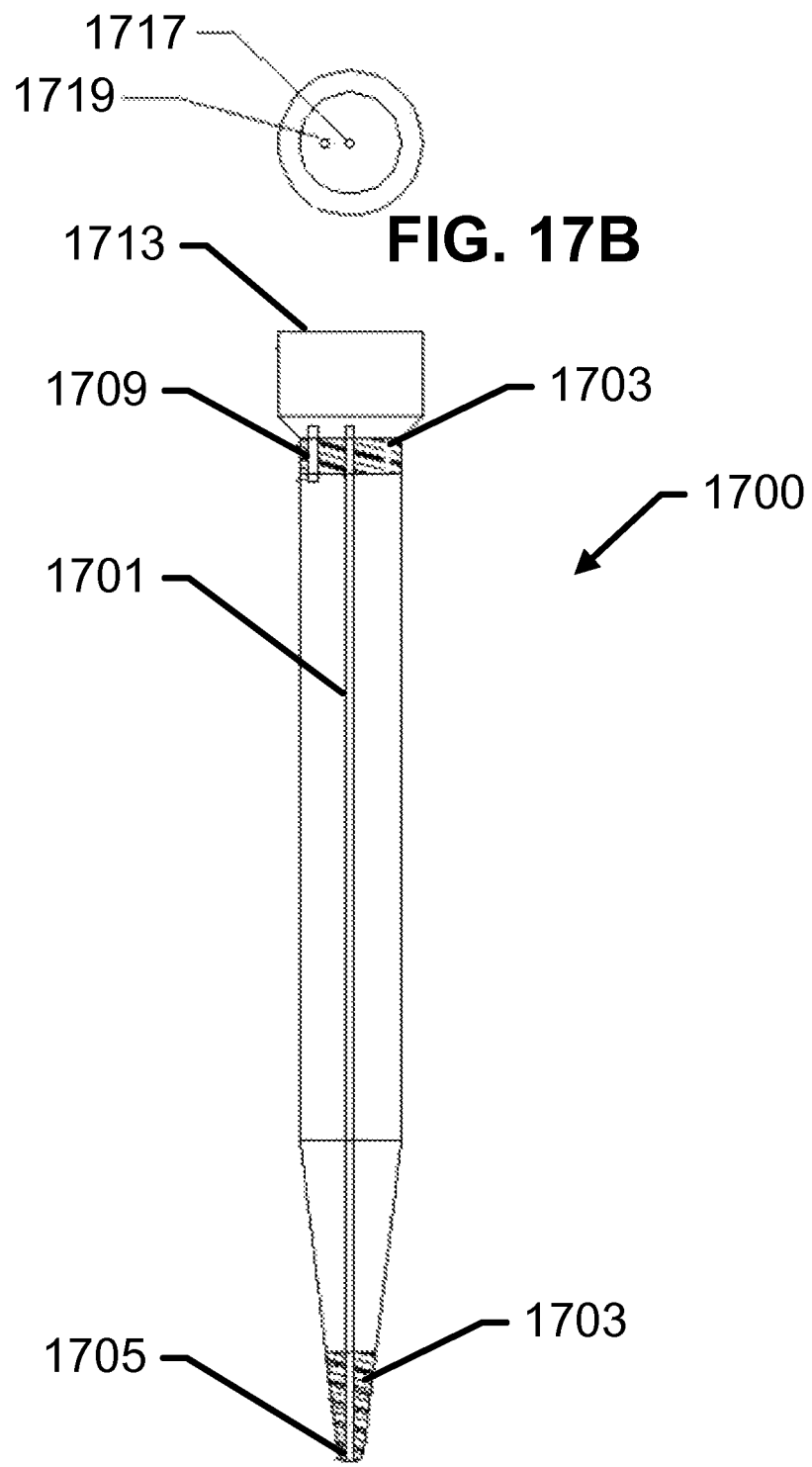

LIQUID TO LIQUID BIOLOGICAL PARTICLE CONCENTRATOR WITH DISPOSABLE FLUID PATH

This U.S. patent Application claims priority to U.S. Provisional Patent Application Ser. No. 61/276,737, filed Sep. 17, 2009, the content of which is hereby incorporated by reference in its entirety into this disclosure.

BACKGROUND OF THE INVENTION

1. Field of the Invention

The invention relates generally to the field of sample preparation. More particularly, the subject invention relates to a method and device for automated concentration of particles for enhancing the sensitivity of subsequent analysis methods.

2. Background of the Invention

The difficulties of detecting and quantifying dilute materials in liquids are well known. Existing systems all begin to fail as analyte concentrations decrease, eventually leading to a non-detect of the analyte at very low concentrations. This poses a significant problem to national security, for example, the postal anthrax attacks of 2001 and the subsequent war on terrorism have revealed shortcomings in the sampling and detection of biothreats. The medical arts are similarly affected by the existing limits of detection, as are the environmental sciences.

The detection limits of existing analytical systems that quantitate particles in solution do not disqualify their use in studying analytes or particles that fall below these limits. Rather, methods are needed for concentration of the particles prior to analysis.

Particle concentration in liquid is traditionally performed using centrifugation. Centrifugal force is used for the separation of mixtures according to differences in the density of the individual components present in the mixture. This force separates a mixture forming a pellet of relatively dense material at the bottom of the tube. The remaining solution, referred to as the supernate or supernatant liquid, may then be carefully decanted from the tube without disturbing the pellet, or withdrawn using a Pasteur pipette. The rate of centrifugation is specified by the acceleration applied to the sample, and is typically measured in revolutions per minute (RPM) or g-forces. The particle settling velocity in centrifugation is a function of the particle's size and shape, centrifugal acceleration, the volume fraction of solids present, the density difference between the particle and the liquid, and viscosity of the liquid.

Problems with the centrifugation technique limit its applicability. The settling velocity of particles in the micron size range is quite low and, consequently, centrifugal concentration of these particles takes several minutes to many hours. The actual time varies depending on the volume of the sample, the equipment used, and the skill of the operator. The nature of centrifugation techniques and of the devices used to perform centrifugation requires a skilled operator, thus making automation and integration into other systems difficult.

Centrifugation techniques are tedious in that they are normally made up of multiple steps each requiring a high level of concentration from the operator. It is common in most microbiology laboratories to process large numbers of samples by centrifugation on a daily basis. The potential for human error is high due to the tedious nature; and as stated earlier automation of these techniques is difficult and costly.

Other concentration techniques have been explored and primarily fall into three technology groups—microfluidic/electrophoretic based, filtration based, and capture based. Each of these techniques has advantages and disadvantages.

Traditional flat filtration methodology is used to capture particles from a liquid onto a flat filter, usually supported by a screen or fritted substrate. Many different methods of filtration exist, but all aim to attain the separation of two or more substances. This is achieved by some form of interaction between the substance or objects to be removed and the filter. The substance that is to pass through the filter must be a fluid, i.e. a liquid or gas. The simplest method of filtration is to pass a solution of a solid and fluid through a porous interface so that the solid is trapped, while the fluid passes through. This principle relies upon the size difference between the particles contained in the fluid, and the particles making up the solid. In the laboratory, this if often done using a Büchner funnel with a filter paper that serves as the porous barrier.

One disadvantage of the physical barrier method of filtration is that the substance being filtered from the fluid will clog the channels through the filter over time. The resistance to flow through the filter becomes greater and greater over time as, for example, a vacuum cleaner bag. Accordingly, methods have been developed to prevent this from happening. Most such methods involve replacing the filter; however, if the filter is needed for a continuous process this need for replacement is highly problematic. Scraping and in-situ cleaning mechanisms may be used, but these can be unnecessarily complex and expensive.

In one example, bacteria may be removed from water by passing them through a filter supported in a Buchner funnel to trap the bacteria on the flat filter. Aerosol particles containing biological materials can also be trapped in the same way. For analysis, the trapped materials are often re-suspended in a known volume of liquid. This allows back-calculation of the original aerosol concentration. One method validated by the Edgewood Chemical Biological Center uses 47 mm glass-fiber filters to capture reference samples for biological analysis. The bacteria are extracted by soaking the filters overnight in 20 mL of buffered saline solution, then vortexed for 3 minutes to disrupt the filter material completely. Subsamples or aliquots of these suspensions are then provided for analysis by viable culture, PCR, or other methods.

Tangential flow filtration is a variant of traditional filtration. This technique is sometimes called side-stream filtration or cross-flow filtration, and most often uses membrane systems to purify proteins. These systems circulate retentate across the membrane surface, which minimizes the fouling of the membrane. This arrangement provides longer membrane use, resulting in higher overall filtration efficiency. This process has been used in processing cell lysate to clean up the fluid for analysis of particular proteins. Millipore Corporation and Pall manufacture tangential flow filter cassettes that may be purchased on commercial order. Tangential flow systems are also used commercially for particles larger than proteins, and on scales larger than in the micron range.

The membrane in a tangential flow system may be a hollow fiber filter. These filters are commercially produced by a few companies, most notably Spectrum Laboratories, Inc. Hollow fiber filters may be constructed and arranged in packages as required for the intended environments of use, such as laboratories, small scale pharmaceutical production companies, or larger scale water treatment facilities.

Fluid Analytics, Inc. of Portland, Oreg. has developed a liquid sample concentrator that utilizes tangential flow across a flat filter and a proprietary controlled sonication method to remove collected particles. The unit has a flow rate of 20 mL/min with a sample volume of up to 20 mL and a concentrated volume of less than about 1 mL. The concentration efficiency is reported as being 90%, but a particle size or type associated with this data is not provided. A unit capable of concentrating into 100 μL is stated as being under development.

Other technologies for concentration of biological particulate matter exist. Sandia National Laboratories, Massachusetts Institute of Technology, and other organizations have developed microfluidic devices that separate and concentrate particles by dielectrophoresis or electrophoresis. These units use microchannels and electric fields to move or collect particles. Sandia has also developed a system that concentrates particles at the interface between two immiscible liquids. Immunomagnetic particles are commercially available for use in the separation and concentration of bacteria.

Various methods exist for concentrating organisms in liquids prior to detection. Historically, the most common method is to enrich the sample in nutrient broth and then cultivate an aliquot of the broth on an agar plate. The biggest disadvantage of this method is the time requirement. It normally takes five to seven days before organisms can be enumerated on the plates. Other concentration methods include various filtration based methods, adsorption-elution, immunocapture, flocculation, and centrifugation. It is problematic that to date no automated methods have been developed that can rapidly concentrate a large volume of water into a very small sample volume and do this task efficiently. In fact most of these methods fail in each of these areas, most notably efficiency of concentration, and ease of use.

A considerable amount of research has been performed using hollow fiber ultrafiltration to concentrate bacteria, viruses, and protozoa from large volumes of water. These methods all use variations of tangential flow or dead end filtration with concentration into water or a water and surfactant solution. Most of the methods described are not automated. Generally these systems are capable of concentrating 10 to 100 L water into 100 to 500 mL of concentrated sample; however, it is further problematic that none of the demonstrated technologies provides concentration into volumes of less than 100 mL. Even this volume is much larger than desired for the best possible detection when the concentrator systems are coupled with downstream detection apparatus. This means that a costly and time-consuming second manual concentration step is required to bring the final sample to the desired volume.

The alternative concentration systems described above, although automated, do not provide significant advantages over traditional centrifugation for many laboratories, including microbiology, biotechnology, and clinical biology laboratories. These laboratories require a high level of certainty that sample to sample contamination does not take place. The alternative, automated concentration systems, have significant fluidics that samples are exposed to and in many cases it is, at best, costly and, at worst, impossible to replace these fluidics lines between samples.

The potential for carryover of particles of interest or signatures from one sample to another and the potential for growth of bacteria within the system fluidics significantly limit their applicability to clinical laboratories. In general, microbiology and biotechnology laboratories have adopted the use of disposable components in nearly all work.

A concentration system with a disposable fluid path that is capable of concentrating biological materials from relatively large volumes of liquids would have significant applicability to clinical diagnostics and microbiology and biotechnology laboratories. Spin columns that contain an ultrafilter or microfilter type membrane filters and can be placed into a centrifuge or in some instances use positive pressure to drive the liquid through are a relatively new device that is now seeing wide spread use in these laboratories.

These centrifugal spin columns overcome the contamination issues associated with other concentration systems and also overcome many of the issues associated with using centrifugation to concentration biological materials; however, the spin columns are costly, due to there complexity, and still require significant manual manipulation and pipetting during operation. A fairly high skill level is also required for their use.

SUMMARY OF THE INVENTION

The present disclosure addresses the problem outlined and advances the art by providing a highly efficient filtration-based concentration system with sample fluidic lines and filter packaged in a disposable tip. All conduits by which the disposable tip attaches to the instrument are combined into a single connection point on the upper end of the tip. To operate the system a new, clean tip is attached to the concentrator unit and the lower opening is dipped into a liquid sample contained in an appropriate sample container and the unit is activated. The sample is then aspirated into the tip where it comes into contact with the filter. The liquid is passed through while particles and molecules larger than the filter pore size are captured and retained. When the entire sample has been processed, the lower opening of the tip is placed into an appropriate sample container and an elution fluid or foam is used to elute the captured material and dispense it in a reduced volume.

Prior to dispensing the concentrated sample, it is also possible to perform wash steps, labeling steps, cell lysis, or other manipulation by pushing or aspirating a small volume of fluid into the fiber lumen drawing it out through the filter wall or leaving it in the fiber lumen for a period of time prior to drawing it out.

In one exemplary embodiment, the present invention is a device for rapid concentration of particles and molecules from a fluid sample. The device includes an opening for aspirating the fluid sample, a filter coupled to the opening, the filter having a porous surface for capture of particles and molecules from the fluid sample, a permeate draw in fluid communication with the filter, and a permeate purge in fluid communication with the filter. The particles and molecules are eluted from the porous surface and dispensed in a reduced fluid volume through the opening.

In another exemplary embodiment, the present invention is a system for rapid concentration of particles and molecules from a fluid sample. The system includes a container holding the fluid sample, a concentrating pipette tip including a filter, a permeate draw, and a permeate purge, the concentrating pipette tip inserted into the fluid sample container, a concentrating unit including a means for aspirating the fluid sample through the concentrating pipette tip, a permeate pump, and a permeate purge, and a fluid dispensing means for collecting a concentrated sample from the concentrating pipette tip. The fluid sample is aspirated through the concentrating pipette tip and integral filter or porous surface, and then the concentrated sample is eluted from the filter and dispensed.

In yet another exemplary embodiment, the present invention is a method for rapid concentration of particles and molecules from a fluid sample. The method includes connecting a concentrating pipette tip to a concentrating unit, the concentrating pipette tip including a filter, a permeate draw, and a permeate purge, the concentrating unit including a means for aspirating the fluid sample through the concentrating pipette tip and integral filter or porous surface, a permeate pump, and a permeate purge, inserting the concentrating pipette tip into a fluid sample, aspirating the fluid sample through the concentrating pipette tip and integral filter or porous surface, eluting a plurality of particles and molecules from the integral filter or porous surface in the concentrating pipette tip, and dispensing a concentrated sample.

BRIEF DESCRIPTION OF THE DRAWINGS

FIGS. 17A and 17B show an alternate configuration for a CPT, according to an exemplary embodiment of the present invention.

DETAILED DESCRIPTION OF THE INVENTION

Figure 1A:
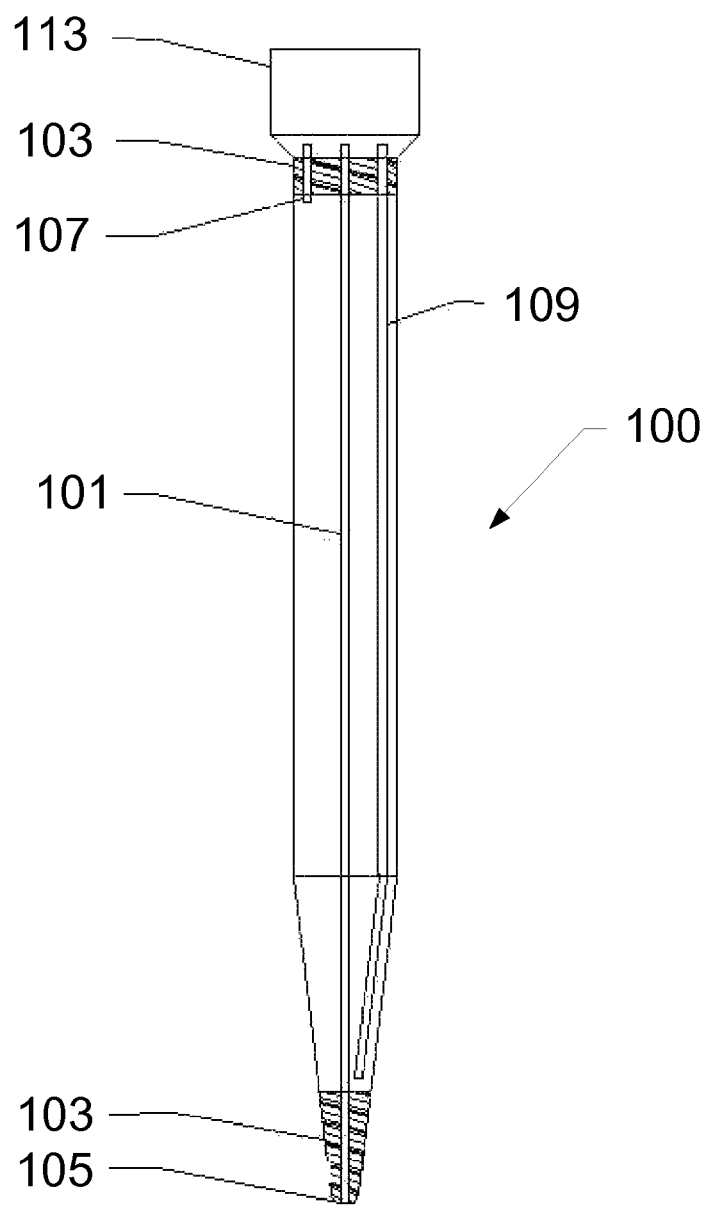
FIGS. 1A and 1B show a concentrating pipette tip (CPT), according to an exemplary embodiment of the present invention.

The present invention is a highly efficient filtration-based concentration system with sample fluidic lines and a filter packaged in a disposable concentrating pipette tip. All conduits by which the disposable concentrating pipette tip attaches to the concentrator unit instrument are combined into a single connection point on the upper end of the concentrating pipette tip. The concentrating pipette tip (CPT) works with a system including a concentrator unit and a liquid sample. To operate the system, a new clean concentrating pipette tip is attached to the concentrator unit and the lower opening of the concentrating pipette tip is dipped into a liquid sample contained in an appropriate sample container and the concentrator unit is activated. The use of a new clean concentrating pipette tip ensures that there is no sample-to-sample carryover. The sample is then aspirated into the CPT where it comes into contact with a filter. The liquid is passed through the filter while particles and molecules larger than the filter pore size are captured and retained. When the entire sample has passed through the filter, removing the fluid and leaving the captured material, the lower opening of the tip is placed into an appropriate sample container and an elution fluid or foam is used to elute the captured material and dispense it in a reduced volume.

Prior to dispensing the concentrated sample, it is also possible to perform wash steps, labeling steps, cell lysis, or other manipulation by pushing a small volume of fluid into the fiber lumen drawing it out through the filter wall or leaving it in the fiber lumen for a period of time prior to drawing it out.

After being dispensed, the concentrated sample may be further concentrated prior to analysis by immunomagnetic separation, electrophoretic or dielelectrophoretic separation techniques, or other microfluidic concentration techniques. In many instances these techniques are useful but are in general not possible with larger volumes or are prohibitively costly or slow when performed on large volumes. By rapidly performing an initial concentration with the CPT the sample volume is reduced to a volume that is more readily handled with these techniques.

It is further possible to apply additional sample preparation techniques to the concentrated sample once dispensed. Additional sample preparation techniques that may be applied include various methods of cell lysis, washing steps, inhibitor or interferent removal techniques, and labeling steps. Reduction of the sample volume prior to performing these techniques routinely improves the speed and efficiency, while reducing the cost of performing these techniques.

Analysis of the concentrated sample may be performed with any number of commonly used traditional analytical or microbiological analysis methods or rapid analysis techniques including rapid microbiological techniques. Analytical techniques of special interest include conventional methods of plating and enumeration, most probable number, immunoassay methods, polymerase chain reaction (PCR), electrochemical, microarray, flow cytometry, biosensors, lab-on-a-chip, and rapid growth based detection technologies to name a few.

Microorganisms including pathogens and spoilage organisms may be concentrated from any number of beverages including fruit juices, vegetable juices, carbonated beverages, alcoholic beverages and from homogenates or liquid samples produced from solid foods. By concentrating large sample volumes in the range of 1 mL to 10 L or more prior to analysis it is possible to rapidly detect microorganisms at levels that were previously only detectable following lengthy culturing of a portion of the sample.

It is further possible to test samples resulting from manual swabbing of surfaces onto wetted swabs, pads, or pieces of filter material often taken for bioterrorism security monitoring. The samples are typically extracted into a volume of liquid resulting in a 2 to 20 mL volume initial sample. Samples like these may be quickly concentrated to much smaller volumes in the range of 4 to 400 µL such that agents may more easily be detected.

In still other aspects, samples may be concentrated for water sampling in search of bioterrorism agents, or in the interest of public health and safety, especially where a sample may contain target agent(s) that are thought to be a threat to the health of humans, animals or plants, causing societal disruption and economic harm. Agricultural products and livestock environments may also be evaluated by the instrumentalities herein disclosed.

Environmental studies that may also benefit from the present invention include many types of sampling and analysis that are performed for the field of environmental study, such as in assessing health effects through research regarding various materials in inhaled particulate matter with aerodynamic diameter below 2.5 microns (PM 2.5) or high altitude aerosol research where low quantities of particulate are collected and must be concentrated for study. These instrumentalities may benefit clean rooms where very low aerosol concentrations of aerosol particles are collected for monitoring that is aimed at source control.

Forensic sciences may also benefit from the present invention by allowing for detection of DNA collected from large surfaces, articles of clothing, air samples, liquids or other forensic type samples. Touch DNA and low-template DNA techniques can be further extended by concentrating large sample volumes into volumes more closely matching the analysis volume.

These types of sampling and analysis are advantageously performed for the fields of homeland security, corporate security, and military force protection. Additional fields of use include medical research and diagnostics. For example, sample concentration is useful in determining if catheter or other medical devices are contaminated with bacteria. These devices routinely become contaminated in the hospital setting. However it is often difficult to determine which device is causing an infection. Concentration of wash fluid from these devices allows for rapid detection of the infecting organism. Sample concentration is useful in cancer research where very low concentrations of experimental drugs in body fluids or urine are the targets of analysis, and in allergy diagnosis where low quantities of specific antigens are the targets of analysis in body fluids. Health effects research may also benefit by determining health effects known to be caused by various materials in inhaled particulate matter with aerodynamic diameter below 2.5 microns (PM 2.5). Benefit is seen in the field of forensic medicine where low concentrations of DNA, toxins, or venoms are the targets of analysis in body fluids. Other aspects of use may include the study of operating rooms for surface extraction and air monitoring of pathogens, as well as pharmaceutical manufacturing where the biological aerosol particulate matter concentration is regulated by the United States Food and Drug Administration.

For the following description, it can be assumed that most correspondingly labeled structures across the figures (e.g., 132 and 232, etc.) possess the same characteristics and are subject to the same structure and function. If there is a difference between correspondingly labeled elements that is not pointed out, and this difference results in a non-corresponding structure or function of an element for a particular embodiment, then that conflicting description given for that particular embodiment shall govern.

In the following figures, there will be shown and described multiple configurations of disposable concentrating pipette tips which may be used to concentrate biological particles into a reduced liquid volume.

FIGS. 1A and 1B show a concentrating pipette tip (CPT) 100, according to an exemplary embodiment of the present invention. FIG. 1A shows a CPT 100 includes an opening 105, a hollow fiber filter 101, a permeate purge 107, and a permeate draw 109. CPT 100, including opening 105, fiber filter 101, permeate purge 107, and permeate draw 109 is replaced between samples, removing the potential for cross contamination within the system. Because the sample is aspirated, concentrated, and dispensed with a single instrument, work flow in the laboratory is improved and the required operator skill level is significantly reduced. Automation of the system through platforms similar to those used in automated pipetting workstations will provide a low-cost alternative to automated centrifuge systems with significantly improved operating and higher efficiencies. Multi-tip concentration systems, such as the present invention, may push the speed of these automated systems an order of magnitude higher.

CPT 100 is a disposable tip that may be constructed by plastic molding techniques. CPT 100 may be, for instance, similar in dimensions to an Eppendorf epT.I.Ps 10 mL tip. CPT 100 includes a connecting portion 113 and an opening 105. Connecting portion 113 allows CPT 100 to be connected to a concentrating unit for operation of CPT 100. Within connecting portion 113, three ports are contained. FIG. 1B shows the three ports, which include a first port 115 connected to permeate purge 107, a second port 117 connected to fiber filter 101, and a third port 119 connected to permeate draw 109. When connected to the concentrator unit second port 117 is in fluidic connection with an elution fluid line originating in the concentrator unit. First port 115 is in fluidic connection with a valve contained within the concentrator unit. Third port 119 is in fluidic connection with a pump contained within the concentrator unit. Opening 105 allows CPT 100 to aspirate a sample into fiber filter 101. Opening 105 provides a small pointed end with a single opening into the lumen of fiber filter 101. CPT 100 also includes potting 103 to secure fiber filter 101, permeate purge 107, and permeate draw 109.

In this configuration, fiber filter 101 is a single hollow fiber filter 101 allowing air to pass through (e.g. microfilter) and is secured into CPT 100 on both ends using potting 103 such that the lumen of fiber filter 101 creates opening 105. Fiber filter 101 may be, for instance, a Spectrum Laboratories, Inc. 100 kD Polysulfone hollow fiber with an internal diameter of 0.5 mm such as those used in the Spectrum Laboratories X1AB-300-04N Module. Connecting portion 113 of fiber filter 101 along with a section of tubing for permeate purge 107 and a section of tubing for permeate draw 109 are all sealed near connecting portion 113 of CPT 100 with potting material 103. In one aspect, fiber filter 101 is one or more hollow fiber filters contained within CPT 100 with CPT 100 being constructed of an impermeable material. Fiber filter 101 or filters and CPT 100 form a permeate chamber between the impermeable wall of CPT 100 and the hollow fiber wall of fiber filter 101.

Hollow fiber filters, such as fiber filter 101, and other membrane type filters are primarily broken into three groups, these are: microfiltration, ultrafiltration, and nanofiltration. Each of these groups is useful for different types of agents being removed from a sample. Nanofiltration filters are not of significant importance here and will not be discussed. Microfiltration refers to those filters with pore sizes of 0.1 micrometer or greater. Ultrafiltration refers to those filters with pore sizes of less than 0.1 micrometer and those in which the pore sizes are generally specified by molecular weight cutoff. Membrane type filters generally are also broken into those specified as hydrophilic and those specified as hydrophobic. In general hydrophobic pore sizes of less than about 0.65 micrometer will not allow aqueous samples to pass through, unless a wetting agent or solvent is used. Hydrophilic filters will readily pass water, but smaller pore sizes, once wet, will not readily allow air to pass until the filter is dried again. In general it is very difficult to dry a wet hydrophilic ultrafilter sufficiently to allow aqueous samples to pass, and additionally, drying ultrafilters can damage the filter resulting in a larger pore size.

Hollow fiber filters made of different materials are used for application specific reasons. Such fibers are commonly made of mixed cellulose esters (ME), polyethersufone (PES), polysulfone (PS), polypropylene (PP) polyacrylonitrile (PAN), hydrophilic polydivinylidene fluoride (PVDF), and other materials such as stainless steel and ceramics. Various advantages and disadvantages accrue to each type of filter. Some design criteria are the size of pores, biocompatibility, smoothness, fouling potential, and physical strength.

Permeate purge 107 is a tube connecting the permeate chamber formed between CPT 100 and the exterior of fiber filter 101 to a permeate valve within the concentrating unit through first port 115. Permeate purge 107 provides a port for allowing air to flow into the permeate chamber. Allowing air into the permeate chamber is necessary so that liquid that collects in the permeate chamber during processing can be drawn out of the permeate and so that negative pressure in the permeate chamber can be quickly returned to atmospheric pressure. In an alternate embodiment the permeate purge is not in fluidic communication with the permeate valve but is rather a small open port. In this way leakage through the port is small enough to allow the permeate pump to draw sufficient vacuum to allow the sample to be processed, but is large enough so that after the sample is processed the remaining fluid can be drawn out of the permeate due to the inward leakage of air. During elution the permeate pump is also large enough to overcome the permeate purge leakage and increase the pressure in the permeate.

Permeate draw 109 provides a means for drawing the sample through fiber filter 101 and removing the permeate from the permeate chamber formed between concentrating tip 102 and the exterior of fiber filter 101. After permeate flows through fiber filter 101 it is removed using permeate draw 109. Permeate draw 109 extends from near the base inside concentrating tip 100 through third port 119 into a pump within the concentrating unit. Permeate is removed from this location until all of the permeate is removed.

First port 115 for permeate purge 107, second port 117 for fiber filter 101, and third port 119 for permeate draw 109 are each contained within connector 113 on the top end of CPT 100. To operate, CPT 100 is attached to the concentrator unit such that first port 115, second port 117, and third port 119 connect with concentrator unit as described above. A fluid sample is aspirated into opening 105 and through the porous surface of fiber filter 101 using a pump contained within the concentrator unit that is connected to permeate draw 109 through third port 119. In this embodiment fiber filter 101 or other membrane type filter is a dry hydrophilic filter, glycerin filled hydrophilic filter, or other filter type that allows air to pass initially and liquid to pass when contact is made, Thus, air is drawn into opening 105 and through the porous surface of fiber filter 101 until fluid is aspirated into opening 105 and making contact with fiber filter 101 passes through the porous surface.

When the entire sample volume has passed through opening 105, the captured particles on fiber filter 101 are eluted by a tangential flush of fiber filter 101 with a known volume of elution buffer or wet foam. Alternatively a backflush of liquid may be used with a secondary tangential sweep with liquid, foam, or a gas. For a number of reasons the use of wet foam is preferred. Two primary reasons for the preference of foam for elution are (1) that a small volume of liquid may be used to create a large volume of foam, thus allowing for smaller elution volumes, and (2) the created foam is much more viscous than the starting surfactant solution, thus allowing for improved passage of the foam through multiple fiber filters. Immediately prior to tangential elution of the filter the valve controlling permeate purge 107 is opened and the pump connected to permeate draw 109 is allowed to continue running so that any remaining fluid is drawn out of the permeate chamber. After the remaining fluid is drawn out the pump controlling permeate draw 109 is turned off and the valve connected to permeate purge 107 is closed. The permeate chamber may then be left at ambient pressure or pressurized to a positive pressure from 0 to 10 psi above ambient pressure. Removing any fluid remaining in the permeate chamber keeps the fluid from being pushed back into the retentate side of fiber filter 101 and pressurizing the permeate keeps wet foam or the elution fluid from passing through fiber filter 101 into the permeate during elution. As the foam proceeds through fiber filter 101, the foam sweeps the concentrate through CPT 100 and out through opening 105. When the foam has exited CPT 100 it quickly collapses back to a liquid, leaving a final concentrated product of a much reduced volume of liquid. This volume can be in a range of less than 5 microliters to 1 milliliter. In its simplest form, the foam may be made in a separate container, and then injected to sweep the sample from CPT 100 into a sample collection port. However, a sample loop may also be used to measure the amount of liquid used to make the foam. In addition to surfactant foams that are generated by mixing air and a surfactant solution the foam may also be generated with a carbonated surfactant solution. Following carbonation, the solution is agitated by dispensing through an orifice, frit, filter, or capillary tube. The surfactant foam extraction methods described here can also be used for extraction and cleaning of other collection surfaces in aerosol samplers and collectors. The use of foam to extract these surfaces can provide a significant increase in extraction efficiency and significant decrease in final sample volume. In a preferred embodiment the foam is produced by holding a buffered surfactant solution under a head pressure of carbon dioxide and then releasing a volume by opening a timed valve. By controlling both the carbon dioxide pressure and the time that the valve is open the volume of liquid dispensed can be tightly controlled.

For hollow fiber concentration pipette tips using ultrafiltration and microfiltration filters, as may be used for concentration of cellular components, DNA, viruses, bacteria, and other pathogens from a liquid sample, the sample is aspirated simply by drawing a negative pressure on the permeate chamber. In this case air is readily drawn through the fiber filter wall and fluid is aspirated into the lumen of the fiber filter where it then passes through the fiber filter wall.

To further improve the efficiency of the concentration pipette tip, a biocompatible surfactant such as Triton X-100 may be added to the feed at low levels, such as 0.1-0.01% by volume. This liquid is an insignificant volumetric addition, but can increase throughput efficiency from the 40% to 65% range to nearly 100%. Buffered surfactant solutions such as 25 mM tris buffered saline (TBS) or phosphate buffered saline (PBS) with 0.01 to 0.1% Triton X-100 or Tween 20 are commonly used in the collection fluids of bioaerosol samplers.

Mechanical shear such as produced by a shaker motor or ultrasonic horn is also used to improved throughput efficiency and processing speed.

Hollow fiber membrane filters used in the CPT can become blinded due to particle loads in the samples being processed. Methods of reducing blinding are well documented and include tangential flow, high-frequency backpulsing (HFB), vibration, and other mechanisms. Tangential flow is the most commonly used, but it cannot be implemented in its standard form in the CPT. In the CPT system, HFB will be implemented using carbon dioxide from the wet foam elution system to create backpressure on the permeate side of the hollow fibers. The backpressure acts to push captured particles out of the filter pores. The backpressure step is performed in very short pulses with short periods of time between, hence the term high-frequency. In tests of seventy minutes of processing apple juice through single, 0.05 μm hollow-fiber CPT, within approximately 10 minutes after processing began the flow rate had dropped by approximately 50% from 2 mL/min to 1 mL/min. HFB was able to restore the flow rate to the initial flow rate of 2 mL/min and able to maintain a flow rate of greater than 1.3 mL/min throughout the remainder of the 70 minute run. Two short periods of time without HFB cycles resulted in a significant drop in the filter flow rate. The second of these gaps was seen at approximately the 47 minute mark and resulted in a drop in filter flow rate of approximately 50%.

Use of combined HFB and tangential flow is well known in industrial separations and provides the most stable flow rate for those systems by allowing the tangential flow to carry away particles removed by HFB. Because traditional tangential flow cannot be implemented on the CPT a novel oscillating tangential flow (OTF) method may be used. By using a metering pump fluidically connected with the inside of the concentration cell hollow fibers to rapidly move fluid up and down, a tangential flow is set up within the system without removing fluid from the hollow fiber bore. Two authors have described the use of vertically oriented vibration of entire hollow fiber concentration cells (Low et al., 2005; Genkin et al., 2006; Low et al., 2008). These systems resulted in significant improvements in filter flow rate with difficult to process samples. Using a metering pump to oscillate the fluid within the CPT rather than oscillating the hollow fibers themselves is seen as more practical implementation of this idea. Implementation of this method is expected to be straightforward and will provide improved sample processing flow rates for difficult to process matrices.

Figure 1B:
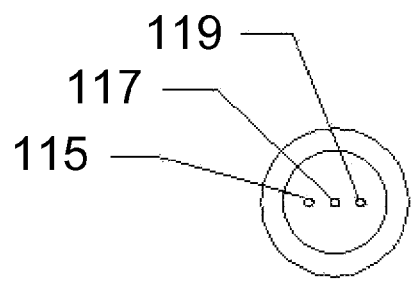
Figure 2A:
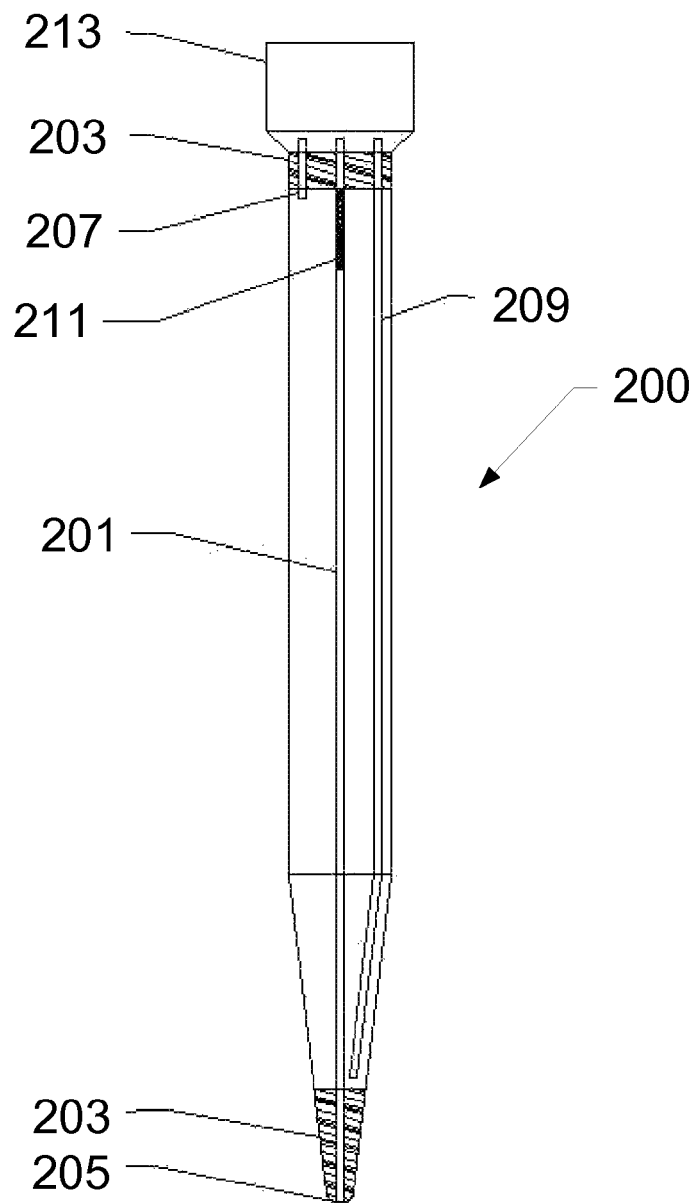
FIGS. 2A and 2B show a similar configuration for a hollow fiber filter that will not allow air to pass through, according to an exemplary embodiment of the present invention.
Figure 2B:
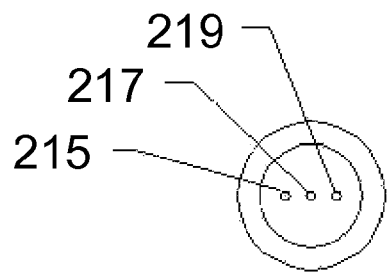

FIGS. 2A and 2B show a similar configuration for a hollow fiber filter 201 that will not allow air to pass through, according to an exemplary embodiment of the present invention. FIG. 2A shows a CPT 200 including an opening 205, a fiber filter 201, a permeate purge 207, and a permeate draw 209. In this configuration fiber filter 201 has an upper hydrophobic vent portion 211 with the lower portion being hydrophilic 201. Hydrophilic filters will readily pass water, but smaller pore sizes, once wet, will not readily allow air to pass until dried again. The addition of hydrophobic vent portion 211 allows air to pass through the vent until the entire hydrophilic hollow fiber 201 has been filled with liquid sample and can thus allow it to pass through. In addition to this advantage, use of hydrophobic vent portion 211 allows air to be introduced into CPT 200 after operation is initiated without filling fiber filter 201 with air and thus stopping flow. Hydrophobic vent portion 211 allows the air to pass and liquid to be drawn into fiber filter 201 again. Connecting portion 213 allows CPT 200 to be connected to a concentrating unit for operation of CPT 200. Within connecting portion 213, three ports are contained. FIG. 2B shows the three ports, which include a first port 215 connected to permeate purge 207, a second port 217 connected to fiber filter 201, and a third port 219 connected to permeate draw 209. The remainder of CPT 200 shown in FIG. 2 is identical in configuration to that shown in FIGS. 1A and 1B. To operate, CPT 200 is attached to the concentrator unit and fluid is aspirated into inlet 205 and through the porous surface of fiber filter 201. When the entire sample volume has passed through inlet 205 the captured particles are eluted by a tangential flush of fiber filter 201 with a known volume of elution buffer or wet foam. Alternatively a backflush of liquid may be used with a secondary tangential sweep with liquid, foam, or a gas.

Figure 3:
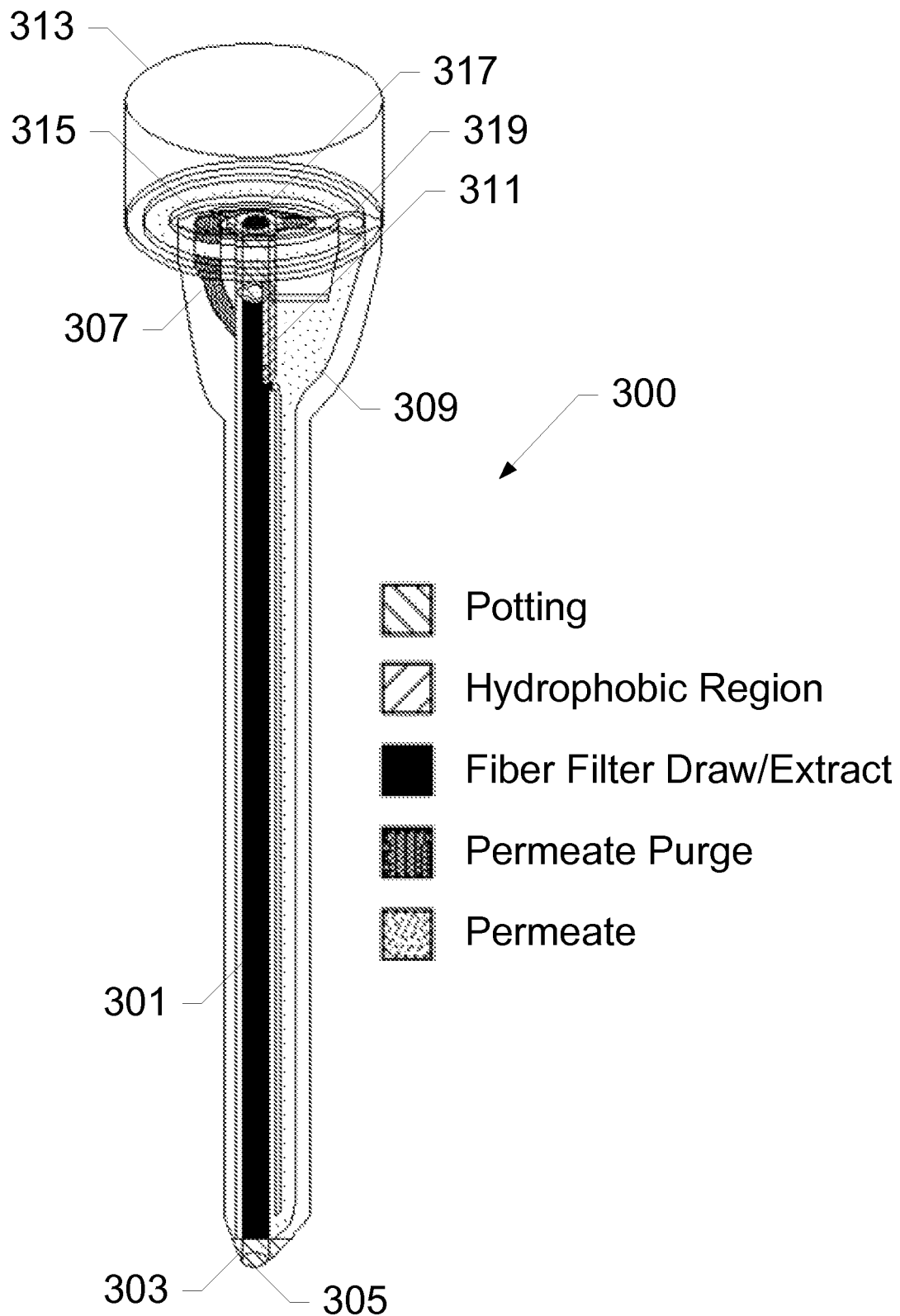
FIG. 3 shows an alternative configuration for connection of a concentrating pipette tip (CPT) to the concentrator unit, according to an exemplary embodiment of the present invention.

FIG. 3 shows an alternative configuration for connection of a concentrating pipette tip (CPT) 300 to the concentrator unit, according to an exemplary embodiment of the present invention. In this configuration annular sections within a main female connector 313 mate with the connector on the concentrator unit's male connector. The annular sections of connectors 315, 317, and 319 allow fluid flow between connectors despite the orientation. The primary advantage of the annular connectors is that CPT 300 does not have to be oriented in a specific way, and may spin or otherwise change orientation during use without disruption. In this particular CPT 300 a hydrophobic flat filter section 311 is used for venting.

Figure 4:
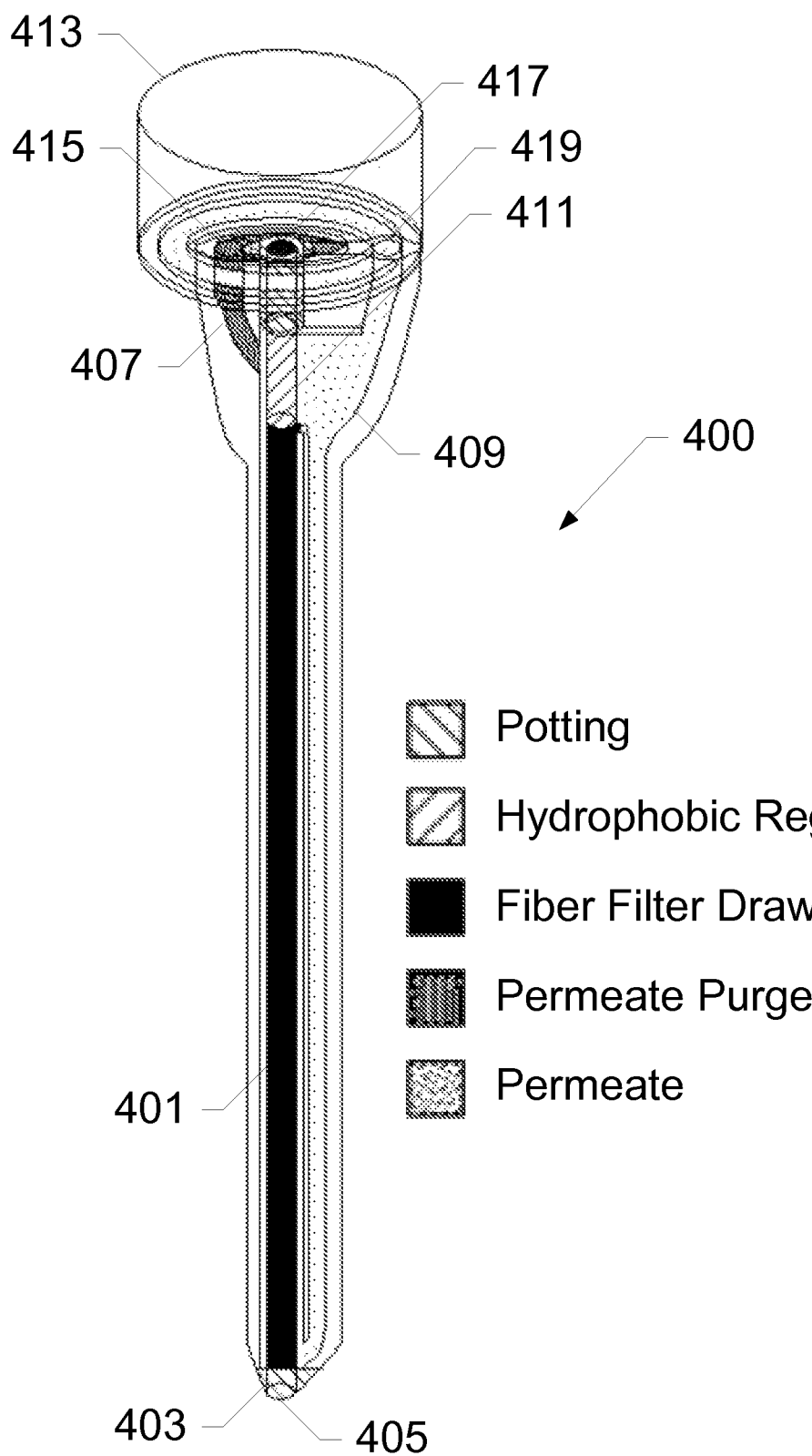
FIG. 4 shows a CPT including an annular configuration for connection to the concentrating unit, according to an exemplary embodiment of the present invention.

FIG. 4 shows a CPT 400 including an annular configuration for connection to the concentrating unit, according to an exemplary embodiment of the present invention. In this configuration annular sections within the main female connector 413 mate with the connector on the concentrator unit's male connector. The annular sections of connectors 415, 417, and 419 allow fluid flow between connectors despite the orientation. FIG. 4 shows the same configuration as that shown in FIG. 3 except that a section of the hollow fiber filter 401 is treated to become a hydrophobic vent layer 411 between the hollow fiber lumen and the permeate chamber. Negative pressure applied to the permeate chamber allows air to be drawn through hydrophobic vent filter 411 and fluid is then aspirated in the fiber lumen of fiber filter 401. When the fluid contacts hydrophobic vent filter 411, flow immediately stops. Hydrophobic vent filter 411 may be a flat filter at the top of hollow fiber 401 between the fiber lumen and the permeate chamber or a hollow fiber filter with an upper hydrophobic section of approximately one inch or less with the remainder of the fiber being hydrophilic in nature.

For concentration tips in which air will not draw through the filter, such as ultrafiltration membrane filters that must be packaged wet, methods of contacting sample fluid with the fiber lumen, while not allowing the fluid to exit the disposable tip and contact the concentrator unit, are disclosed. The first method uses a section of hydrophobic vent filter as discussed in FIG. 2 and FIG. 4.

Another method for contacting fluid with the hollow fiber is by using a syringe pump connected to the fiber lumen to draw a volume of air into the syringe body equivalent to the internal volume of the fiber lumen thereby aspirating liquid into the fiber lumen of the fiber filter. In this way fluid does not pass above the disposable tip, but stops at or near the top of the hollow fiber filter.

Another method for contacting fluid with the hollow fiber filter is by using a pump to draw a volume of air out of the fiber lumen and using an optical or other sensor to stop the fluid flow at the top of the hollow fiber filter. An optical sensor can be attached to the concentrator device, rather than to the disposable tip, and monitor a clear section of the disposable tip above the hollow fiber filter. In this way fluid does not pass above the disposable tip.

Another method of contacting fluid with the hollow fiber filter is by dispensing a volume of clean dilution fluid from the concentrator device into the hollow fiber filter and out of the opening and into the sample container. In this way the entire retentate side of the hollow fiber is filled with fluid and the permeate pump can now be activated to draw the sample into the CPT.

Figure 5:
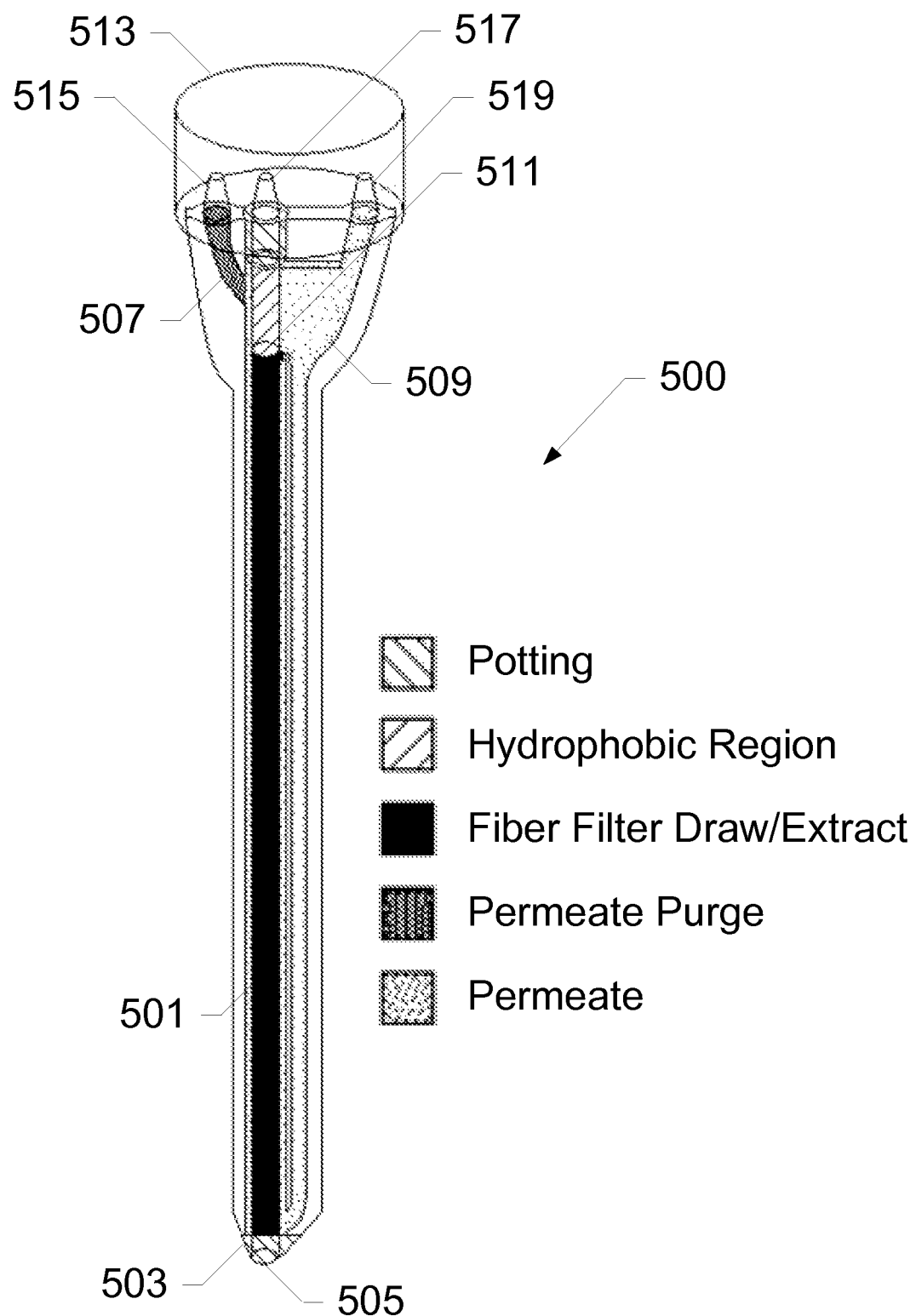
FIG. 5 shows a CPT having pin type connectors, according to an exemplary embodiment of the present invention.

FIG. 5 shows a CPT 500 having pin type connectors 515, 517, and 519, according to an exemplary embodiment of the present invention. CPT 500 also includes a connector 513, a permeate purge 507, a permeate draw 509, and a hollow fiber filter 501. The CPT in FIG. 5 has a configuration like that shown in FIG. 3, except that the fluidics connections are through three pin type connectors as opposed to the annular connections. Though these connections require a specific orientation, they are more reliable and cost-efficient than the annular connections of FIG. 3.

Figure 6:
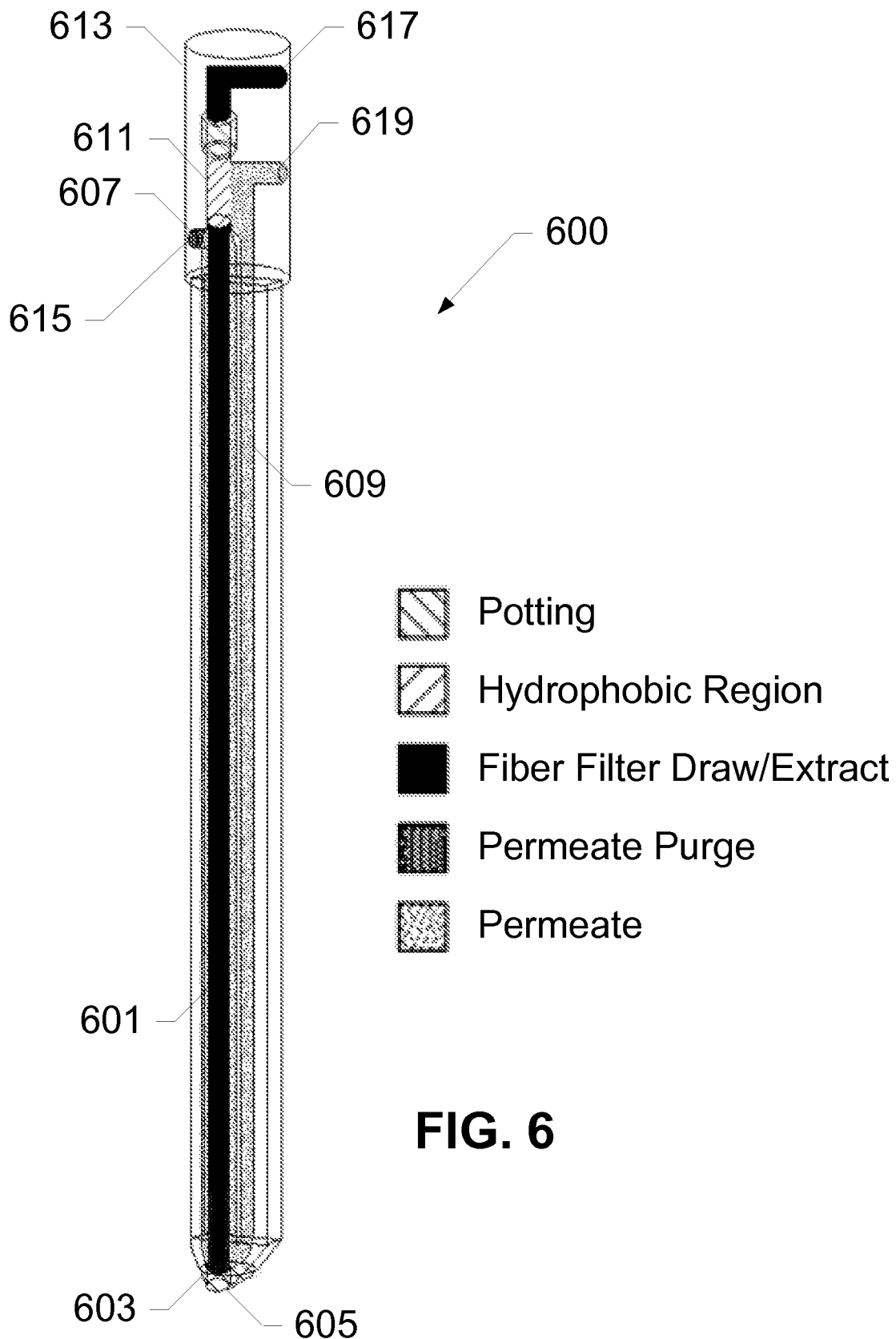
FIG. 6 shows a CPT including a primary male connector, according to an exemplary embodiment of the present invention.

FIG. 6 shows a CPT 600 including a primary male connector 613, according to an exemplary embodiment of the present invention. CPT 600 also includes a hollow fiber filter 601, a permeate purge 607, and a permeate draw 609. Connector 613 includes fluidics connections 615, 617, and 619 at various lengths from the top end. This tip connects to a female connector with integrated annular connections on the concentrator unit. Hollow fiber filter 601 includes a hydrophobic vent filter 611 near the top.

Figure 7:
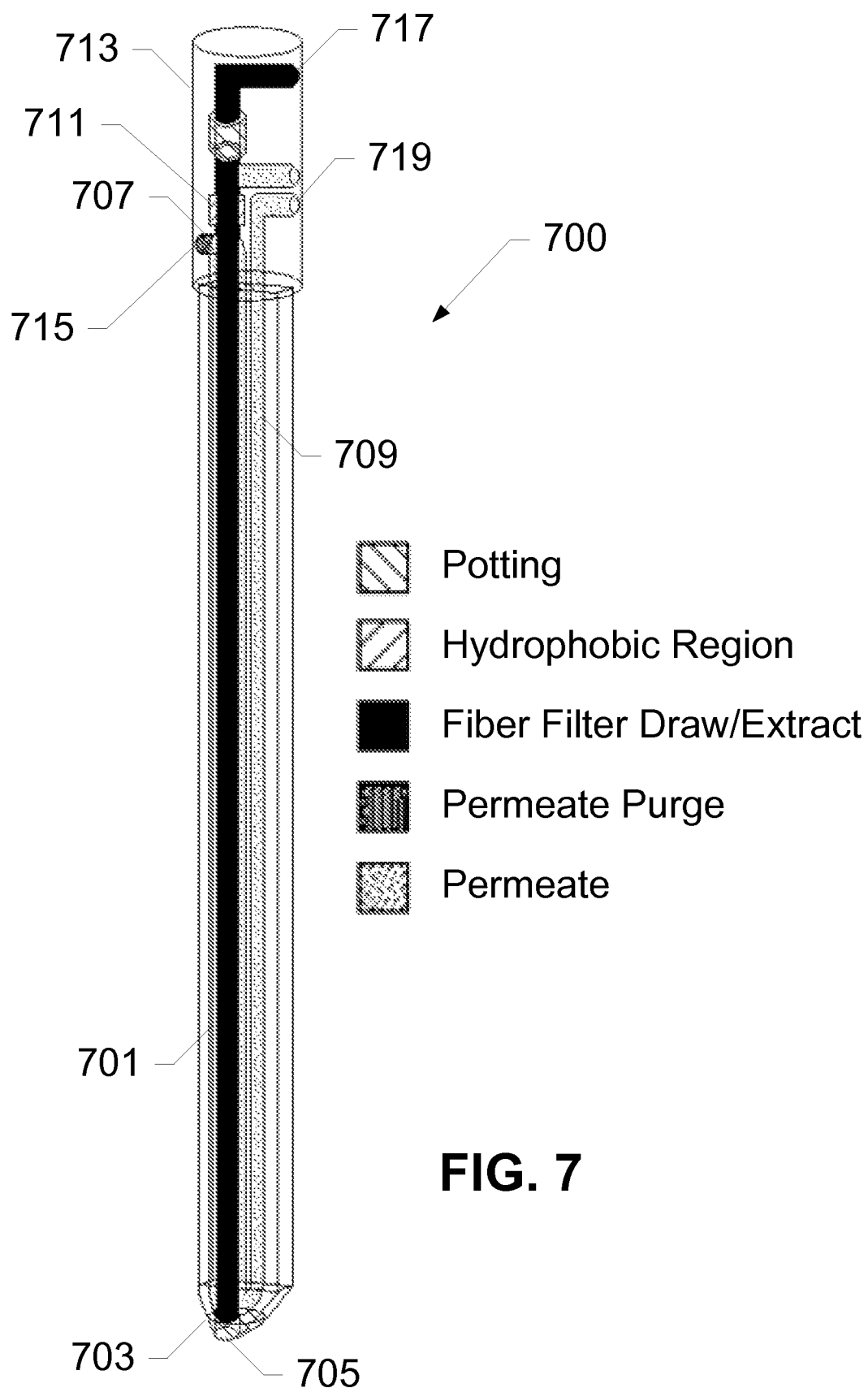
FIG. 7 shows a CPT including a primary male connector, according to an exemplary embodiment of the present invention.

FIG. 7 shows a CPT 700 including a primary male connector 713, according to an exemplary embodiment of the present invention. CPT 700 also includes a hollow fiber filter 701, a permeate purge 707, and a permeate draw 709. Connector 713 includes fluidics connections 715, 717, and 719 at various lengths from the top end. CPT 700 connects to a female connector with integrated annular connections on the concentrator unit. Hollow fiber filter 701 is similar to the hollow fiber filter of FIG. 6, with the exception that the hydrophobic vent filter is replaced with an integrated conductive sensor 711 to assist in startup.

Figure 8:
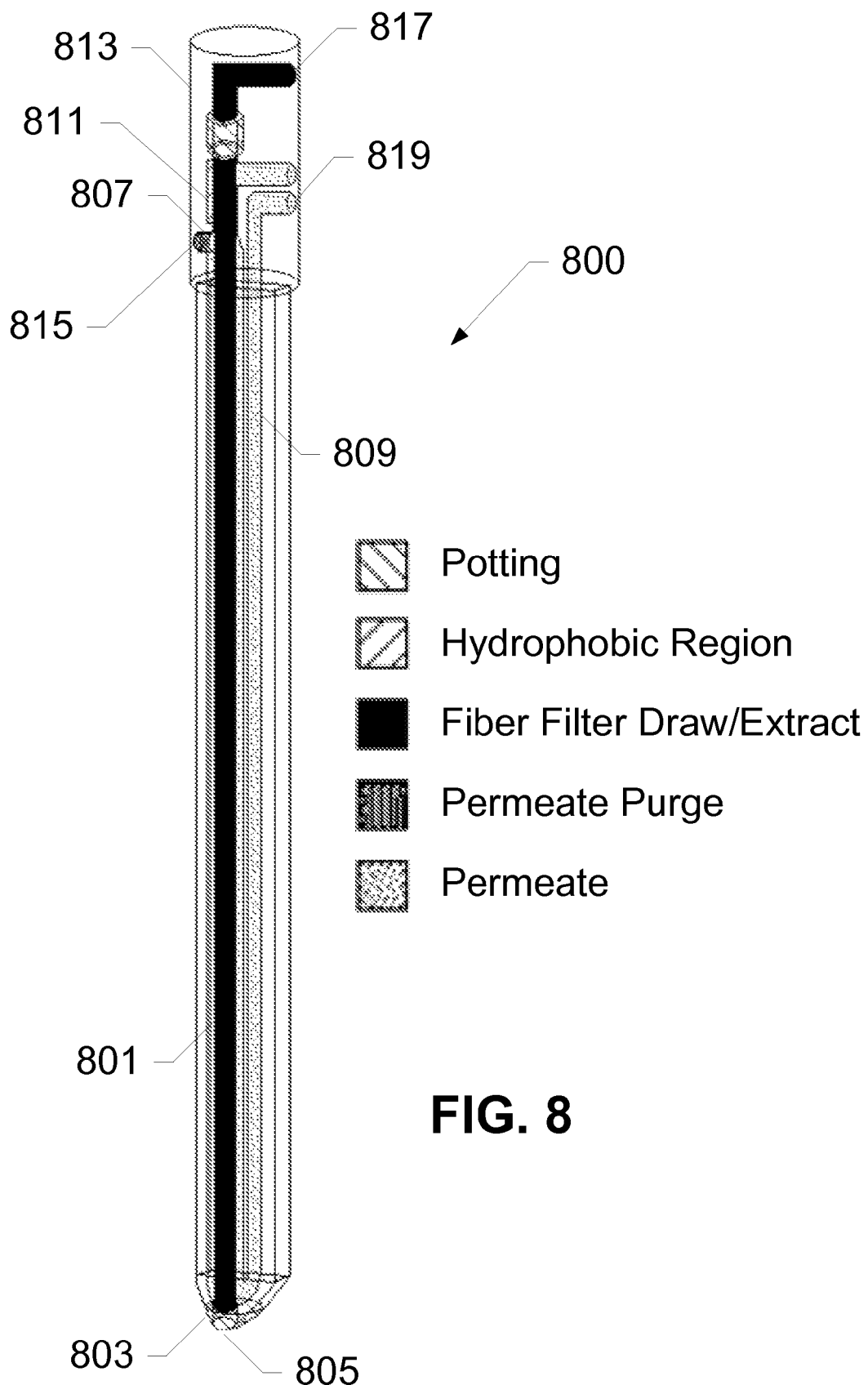
FIG. 8 shows a CPT including a primary male connector, according to an exemplary embodiment of the present invention.

FIG. 8 shows a CPT 800 including a primary male connector 813, according to an exemplary embodiment of the present invention. CPT 800 also includes a hollow fiber filter 801, a permeate purge 807, and a permeate draw 809. Connector 813 includes fluidics connections 815, 817, and 819 at various lengths from the top end. CPT 800 connects to a female connector with integrated annular connections on the concentrator unit. Hollow fiber filter 801 is similar to the configuration shown in FIG. 7, with the exception that the conductive sensor is replaced with an optical sensor section that allows for an optical fluid sensor 811 within the concentrator unit to sense the fluid location.

Figure 9:
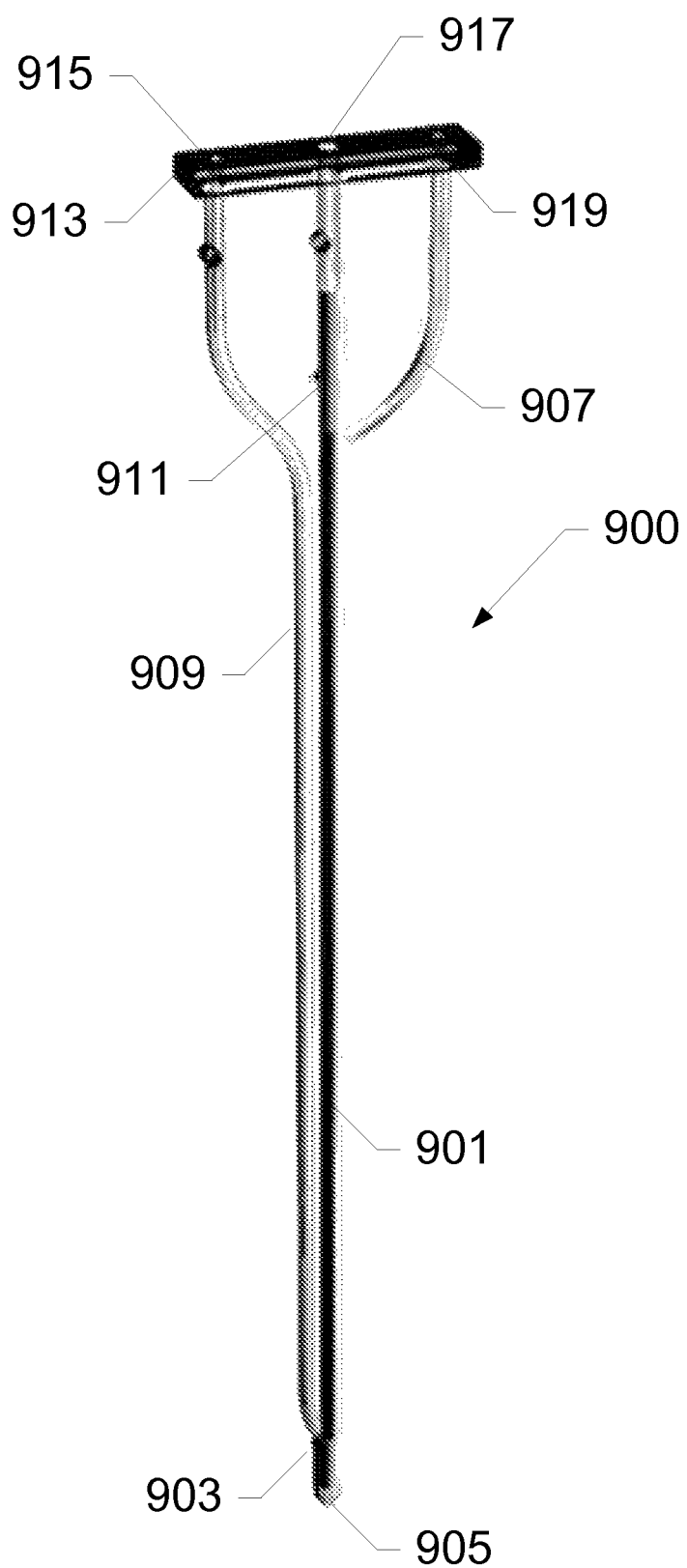
FIGS. 9-11 show one configuration for a CPT, according to an exemplary embodiment of the present invention.
Figure 10:
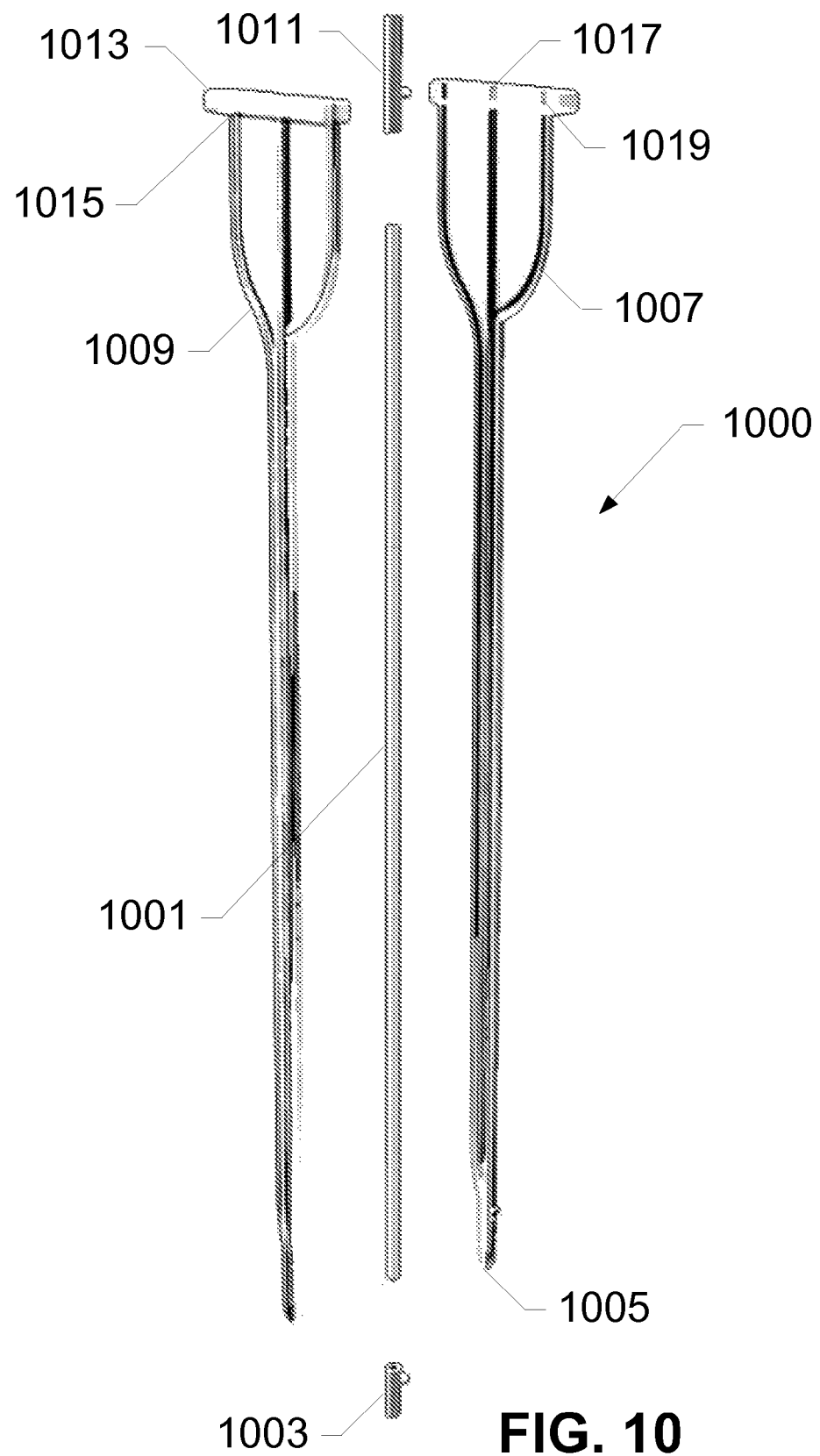
Figure 11:
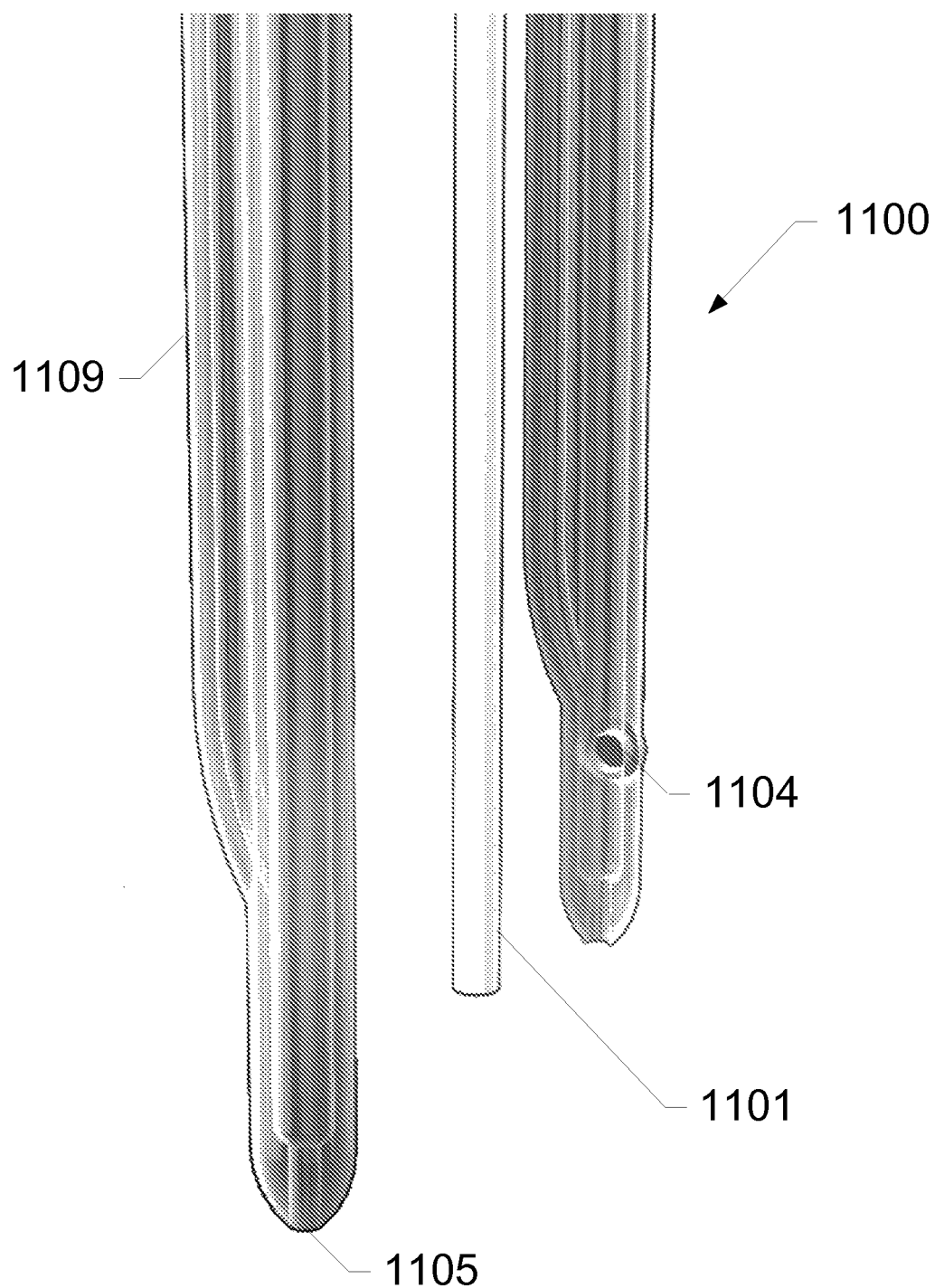

FIGS. 9-11 show one configuration for a CPT, according to an exemplary embodiment of the present invention. FIG. 9 shows a complete CPT 900. FIG. 10 shows an exploded view of CPT 1000. FIG. 11 shows the port used for potting the lower end of the fiber during production.

FIG. 9 shows a complete CPT 900, according to an exemplary embodiment of the present invention. CPT 900 includes a connector 913, a hollow fiber filter 901, a permeate purge 907, and a permeate draw 909. Connector 913 includes fluidics connections 915, 917, and 919.

FIG. 10 shows an exploded view of a CPT 1000, according to an exemplary embodiment of the present invention. Two halves join to make a connector 1013, a permeate purge 1007, a permeate draw 1009, a throughbore for a hollow fiber filter 1001, a hydrophobic vent 1011, and potting 1003. CPT 1000 is snapped together using fasteners. There are many other ways of connecting the two halves that will become apparent to those having skill in the art upon reading this disclosure.

FIG. 11 shows a potting port 1104 for a CPT 1100, according to an exemplary embodiment of the present invention. Once assembled, potting port 1104 allows the user to put potting into the tip of CPT 1100 where it holds hollow fiber filter 1101 in place. Potting is injected with a syringe or other utensil capable of inserting potting into potting port 1104. A machine assembling the concentrating pipette tip may also employ a syringe or other utensil to insert the potting.

Figure 12:
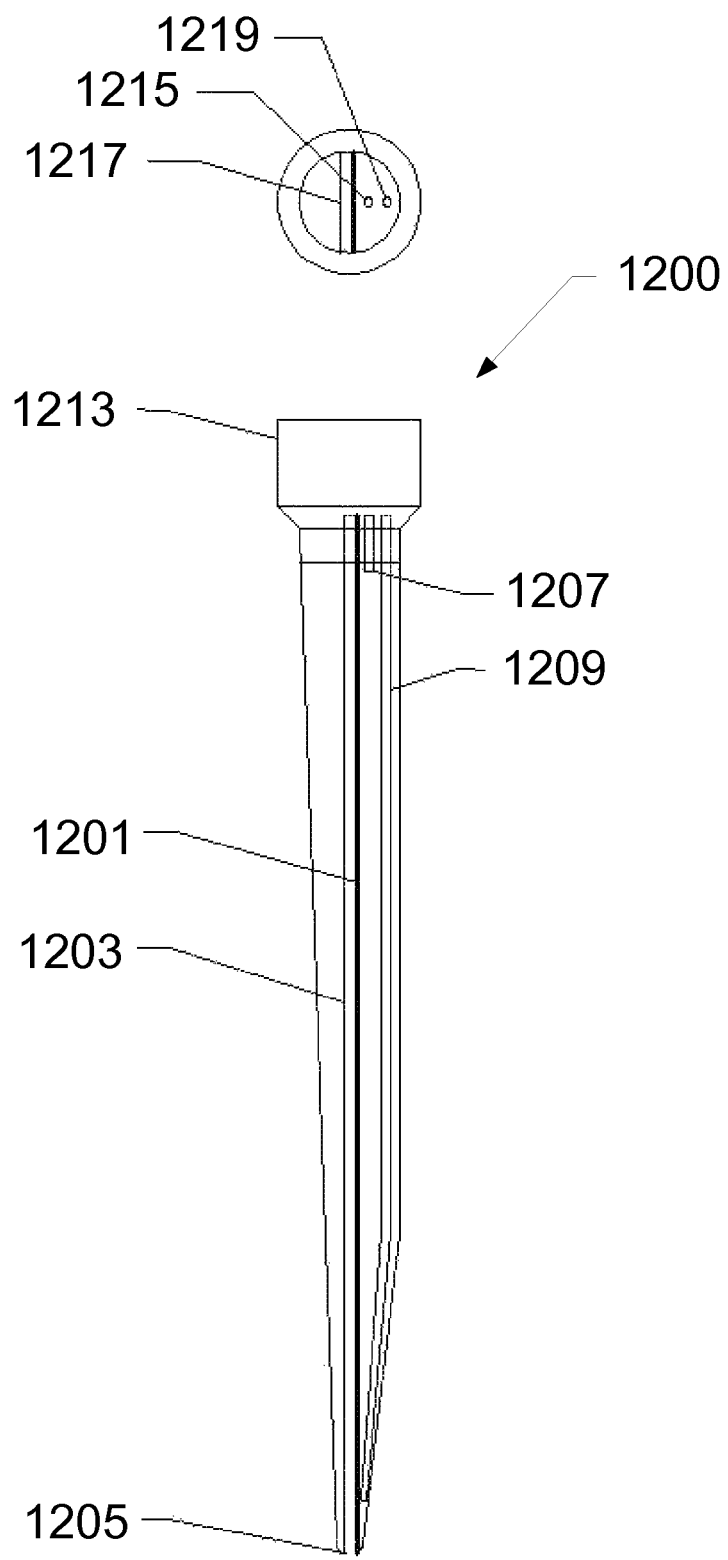
FIG. 12 shows another potential configuration for a CPT, according to an exemplary embodiment of the present invention.

FIG. 12 shows another potential configuration for a CPT 1200, according to an exemplary embodiment of the present invention. A configuration for a disposable concentrating tip uses a flat porous surface 1201 to divide the tip longitudinally into a permeate side and a side containing a retentate channel 1203. Retentate channel 1203 is enclosed on one longitudinal side by porous surface 1201 and on three sides by the impermeable walls of the tip. Channel 1203 is open on both ends; forming a bottom opening 1205 of the CPT 1200 and the retentate port 1217 contained within connector 1213. The permeate side contains a tube to contain permeate purge 1207 and tube to contain permeate draw 1209. Openings for permeate purge 1207 and permeate draw 1209 are contained within their respective ports 1215 and 1219 contained within connector 1213. To operate, CPT 1200 is attached to the concentrating unit and fluid is aspirated into CPT 1200 and through porous surface 1201. When the entire sample volume has passed through CPT 1200, the captured particles are eluted by a tangential flush of flat porous surface 1201 with a known volume of elution buffer or wet foam. Alternatively a backflush of liquid may be used with a secondary tangential sweep with liquid, foam, or a gas.

Figure 13:
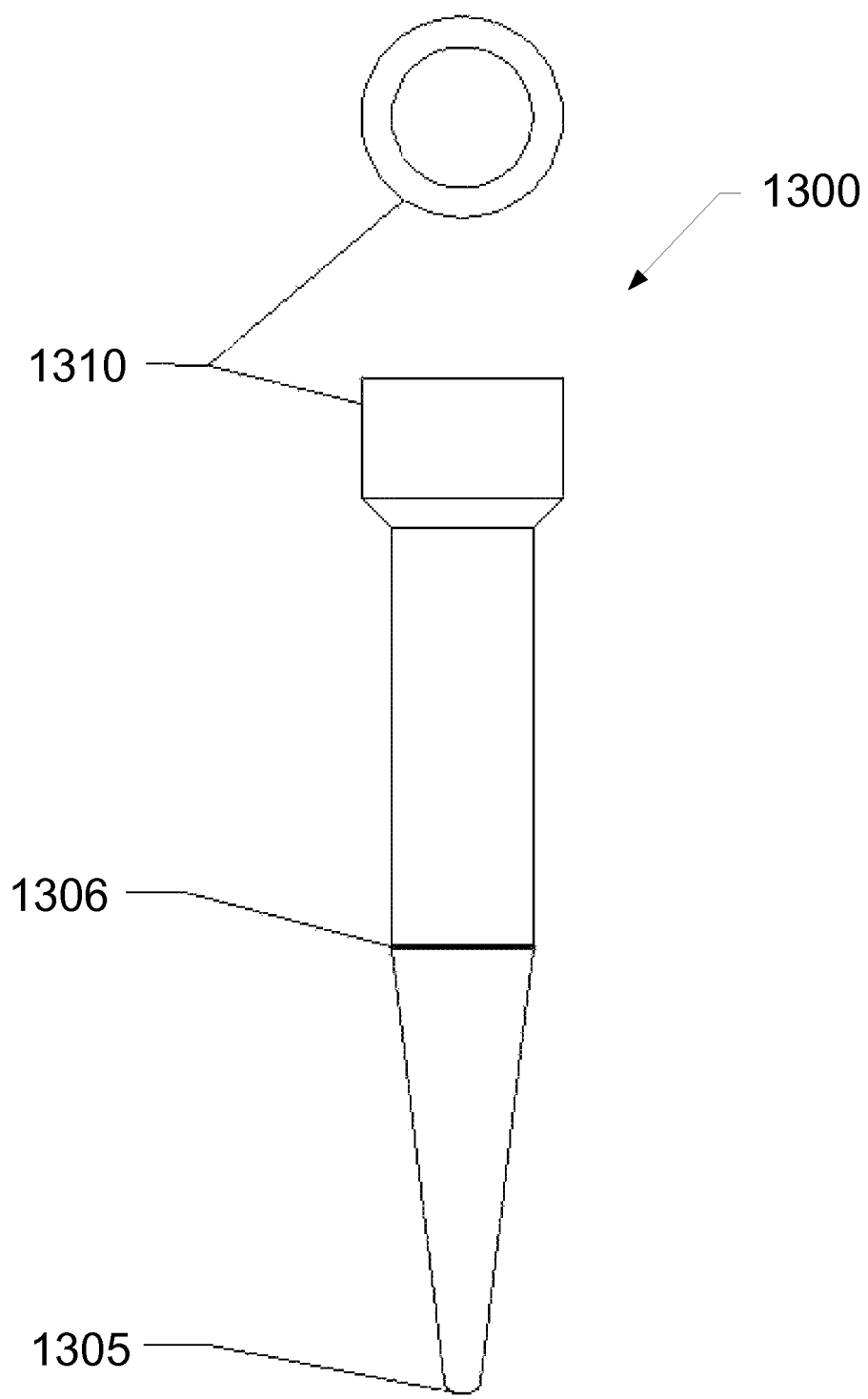
FIG. 13 shows a configuration for a CPT with a flat porous surface dividing the tip into an upper portion and a lower portion with an opening at the lower end and a connector at the upper end, according to an exemplary embodiment of the present invention.

FIG. 13 shows a configuration for a CPT 1300 with a flat porous surface 1306 dividing the tip into an upper portion and a lower portion with an opening 1305 at the lower end and a connector 1310 at the upper end, according to an exemplary embodiment of the present invention. Porous surface 1306 may be a depth filter, electret filter, microsieve, charged filter, membrane, porous media or other porous surface. To operate, CPT 1300 is attached to the concentrator unit and fluid is aspirated into opening 1305 and through porous surface 1306. When the entire sample volume has passed through opening 1305 then the captured particles are eluted by backflushing the filter with a know volume of wet foam or liquid.

Figure 14A:
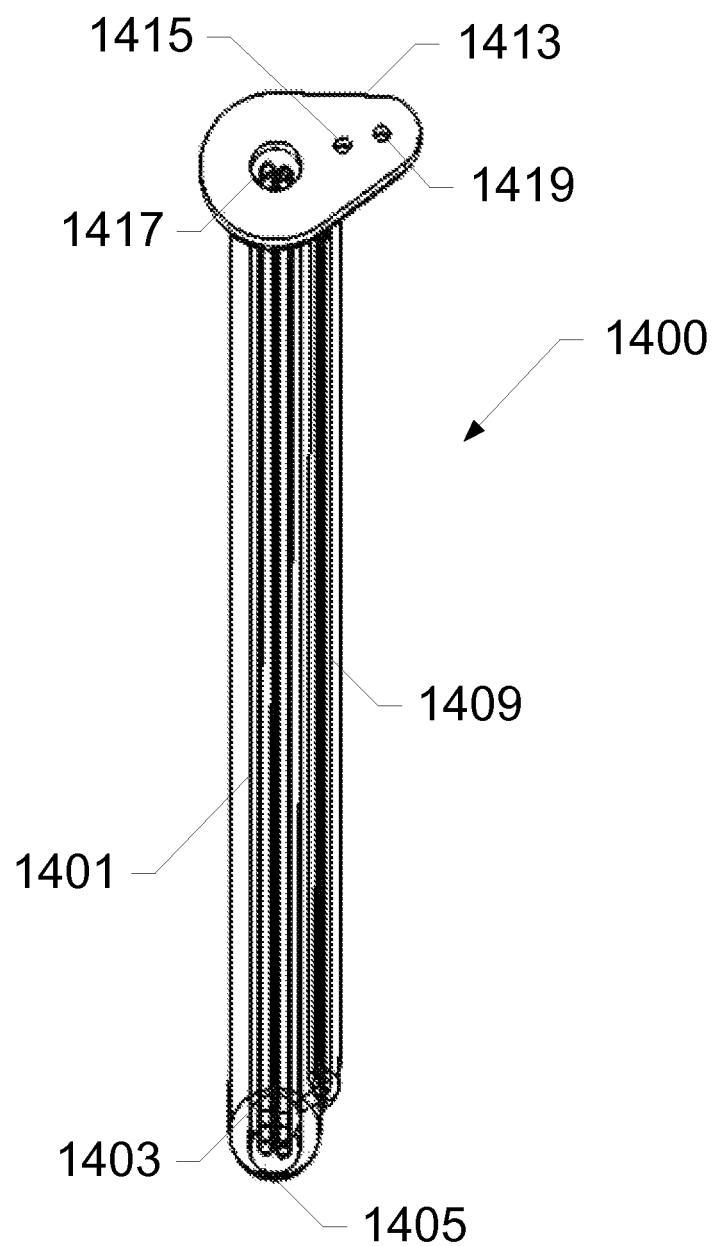
FIGS. 14A-C show another configuration for a CPT, according to an exemplary embodiment of the present invention.

FIG. 14A shows another configuration for a CPT 1400, according to an exemplary embodiment of the present invention. FIG. 14A shows a CPT 1400 including a connector 1413, two hollow fiber filters 1401, a permeate draw 1409, and potting 1403 to secure the hollow filter. Connector 1413 further includes fluidic connections 1415, 1417, and 1419. Hidden from view underneath connector 1413 is a permeate purge. The permeate purge can be more clearly seen in FIG. 14B.

Figures 14B, 14C:
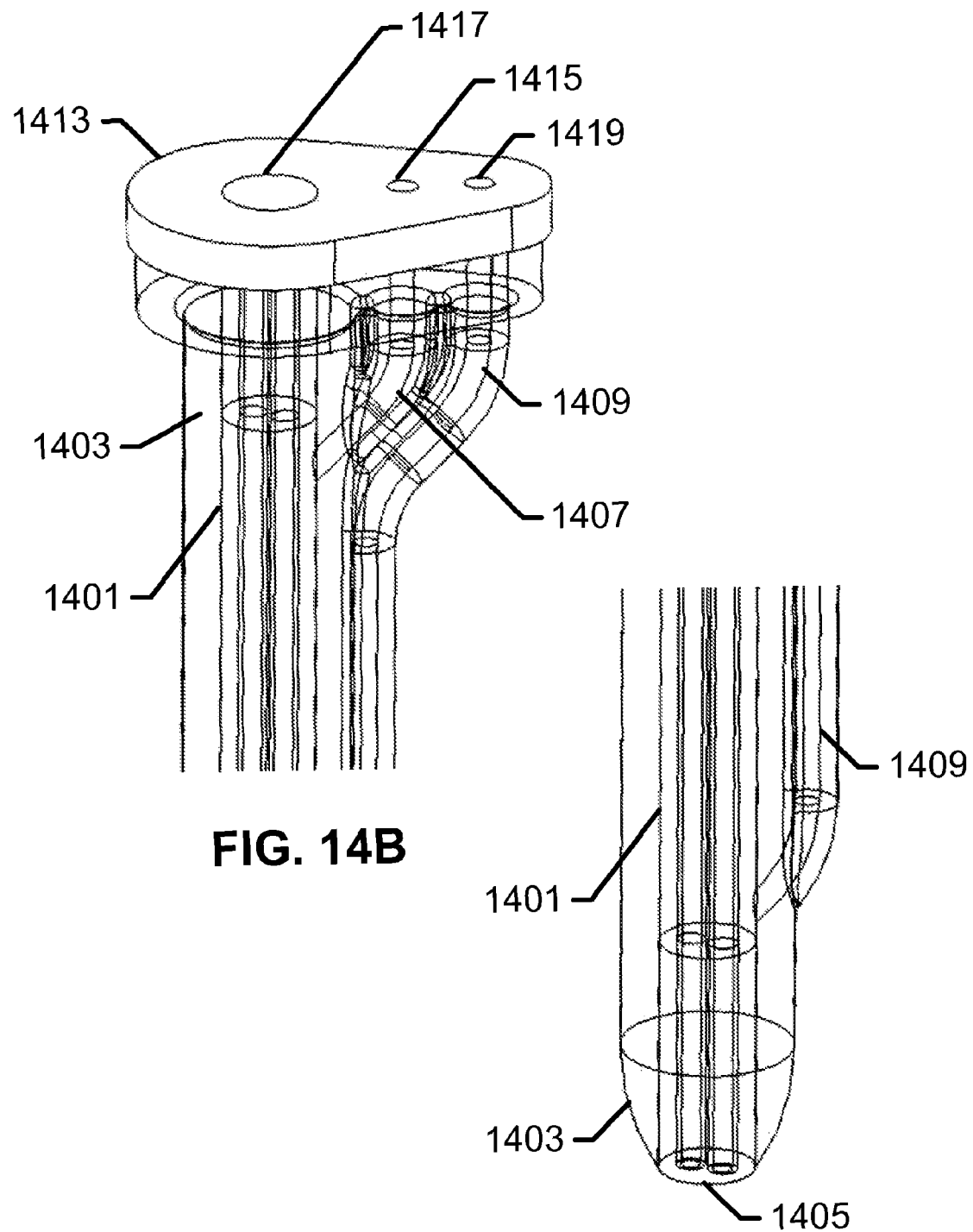

FIG. 14B shows the end having connector 1413 of the CPT, according to an exemplary embodiment of the present invention. Connector 1413 includes fluidic connections 1417, 1415, and 1419. Fluidic connection 1415 connects with permeate purge 1407 and a permeate purge line of the concentrating unit. Fluidic connection 1419 ports fluid from permeate draw 1409 to a permeate pump of the concentrating unit. Fluidic connection 1417 ports extraction foam or fluid from the concentrating unit to the hollow fiber filter. Potting 1403 secures hollow fibers 1401 into the CPT.

FIG. 14C shows the end having opening 1405 of the CPT, according to an exemplary embodiment of the present invention. Opening 1405 receives fluid from a sample for concentration. Hollow fiber filter 1401 is held in place by potting 1403 at opening 1405. Permeate draw 1409 draws permeate from the sample.

Figure 15:
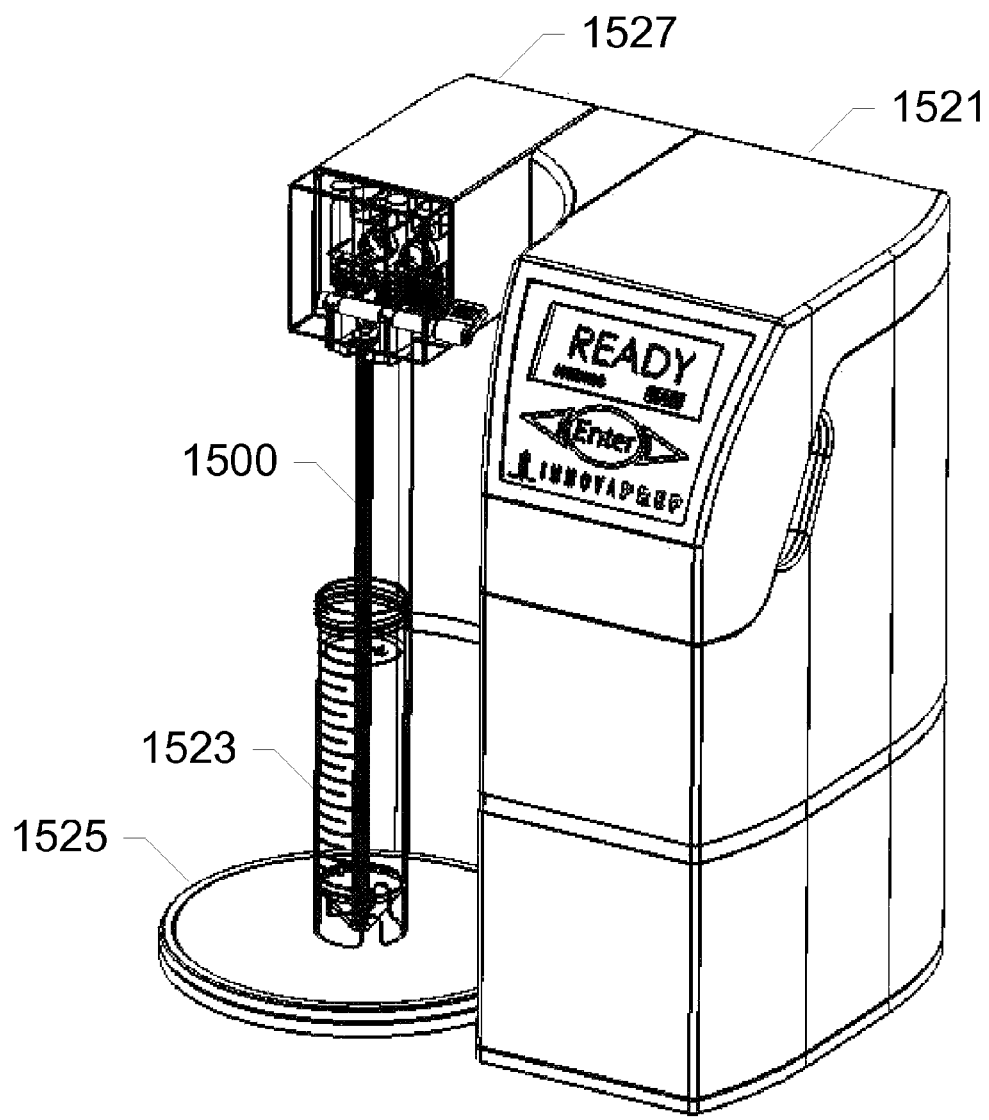
FIG. 15 shows a concentrating unit gathering a sample through a CPT, according to an exemplary embodiment of the present invention.

FIG. 15 shows a concentrating unit 1521 gathering a sample 1523 through a CPT 1500, according to an exemplary embodiment of the present invention. Sample 1523 is placed on a tray 1525 while arm 1527 is raised. CPT 1500 is attached to arm 1527, and arm 1527 is lowered so that CPT 1500 is submerged in sample 1523. An operator then starts concentrating unit 1521, and the sample is aspirated into CPT 1500.

When the entire sample has been processed the concentrated sample is dispensed into a sample container.

Figure 16:
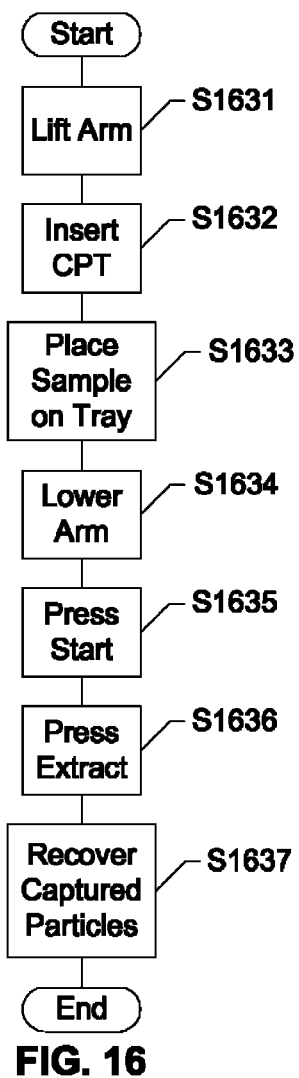
FIG. 16 shows a method of using a concentrating unit having a CPT, according to an exemplary embodiment of the present invention.

FIG. 16 shows a method of using a concentrating unit having a CPT, according to an exemplary embodiment of the present invention. First, the arm is raised S1631 so that the CPT can be inserted into the arm S1632. A lever is pushed and the CPT is pushed into the CPT port. The CPT port contains a gasketed sealing surface and a spring loaded surface to hold the CPT ports in place and seal the connections from leakage. This sealing surface contains connectors for the three CPT connecting ports. Next, the sample is placed on the tray S1633. The arm of the concentrating unit is then lowered S1634, dipping the CPT into the bottom of the sample, but without blocking the fiber opening. A user presses start to turn on the vacuum S1635 and the sample begins concentrating within the CPT. Once the sample has been pulled through the CPT, a user can stop the sample processing by pressing a button on the concentrator or the concentrator will detect stoppage of flow through the tip and automatically stop the sample processing. A user may then choose to dispense the concentrate into the original sample container or a user may replace the original sample container with a new extraction sample container. The user then presses the extraction button S1636 activating the extraction cycle. The extraction process is then activated to recover the capture particles S1637 into a concentrated final volume.

In one aspect, the porous surface used for capturing the particles is a flat fibrous type filter, a flat membrane type filter, or a flat porous surface such as a microsieve or nucleopore filter. This flat filter may be positioned lengthwise in the disposable tip such that it separates the interior space of the disposable tip into a retentate side and a permeate side. Capture of the particles of interest and recovery with the elution fluid are performed in much the same way as with the hollow fiber filter disposable tip described above with the exception that capturing and recovery of particles takes place on the retentate side of the flat membrane rather than within the hollow fiber filter lumen. The length of the retentate, in this case, is enclosed on one wall by the porous surface and on the remaining three walls by the impermeable walls of the disposable tip. In the case of the configuration and the hollow fiber filter configuration the particles of interest are recovered by sweeping through the retentate, in a direction tangential to the porous surface, with a foam or liquid elution fluid. Alternatively the particles may be recovered by backflushing the porous surface with a fluid or by any combination of backflushing or tangential flushing with a liquid or gas.

In another configuration the porous surface used for capturing the particles is a filter or porous surface dividing the disposable tip into to a lower retentate reservoir and an upper permeate reservoir. In this case particles of interest are captured onto the bottom side and into the structure of the porous surface. Said particles are then recovered by backflushing the porous surface with a wet foam or liquid elution fluid. The preferred embodiment of this configuration is for charged filters with recovery by way of backflushing with wet foam.

FIGS. 17A and 17B show an alternate configuration for a CPT 1700, according to an exemplary embodiment of the present invention. FIG. 17A shows a CPT 1700 including an opening 1705, a fiber filter 1701, and a permeate draw 1709. In this embodiment, there is not a permeate purge. According to this embodiment, permeate draw 1709 is shortened, similar to the length of the permeate purge in other embodiments. Each of fiber filter 1701 and permeate draw 1709 is secured within CPT 1700 with potting 1703. A connecting portion 1713 allows CPT 1700 to be connected to a concentrating unit for operation of CPT 1700. Within connecting portion 1713, two ports are contained. FIG. 17B shows the two ports, which include a port 1717 connected to fiber filter 1701 and a port 1719 connected to permeate draw 1709. During operation, the permeate chamber fills with fluid and stays full throughout the sample processing. During elution of fiber filter 1701, instead of pressurizing the permeate chamber a valve is closed on permeate draw 1709 leaving a liquid filled permeate chamber. During elution it isn't necessary to pressurize the permeate chamber because there is void space for the fluid to go into on the permeate side, so the elution fluid or foam will not readily pass through fiber filter 1701.

In one aspect of this configuration, instead of using a permeate valve within the concentration unit a check valve is integrated into the permeate draw 1709 such that a single connection can be used for the CPT. In this way, a sample is aspirated into the CPT and through the filter by applying a permeate pump to connecting portion 1713. The permeate chamber fills will fluid and stays throughout the sample processing. During elution of fiber filter 1701, the elution fluid or foam is dispensed into connecting portion 1713 which causes the check valve with in permeate draw 1709 to close causing the elution fluid or foam to pass through fiber filter 1701.

In exemplary embodiments, after preparation of a blood sample, by removal of blood components such as red blood cells, the present invention may be used to concentrate bacterial pathogens within the blood.

The foregoing instrumentalities have significant utility in medical, environmental, or security applications. For example, concentration in the manner described facilitates aerosol sampling for pathogens or bioterrorism threat agents that can withstand being placed in a liquid sample for analysis. A list of such pathogens may be provided, for example, as recognized by the Center for Disease Control (CDC). These organisms may be studied using conventional techniques that are facilitated by the concentration of samples as described above.

TABLE 1

CDC CATEGORY A AND B BIOTERRORISM AGENTS LIST

CATEGORY A

Anthrax (*Bacillus anthracis*)
Botulism (*Clostridium botulinum* toxin)
Plague (*Yersinia pestis*)
Smallpox (Variola major)
Tularemia (*Francisella tularensis*)
Viral hemorrhagic fevers (filoviruses [e.g., Ebola, Marburg] and arenaviruses [e.g., Lassa, Machupo])

CATEGORY B

Brucellosis (*Brucella* species)
Epsilon toxin of *Clostridium perfringens*
Food safety threats (e.g., *Salmonella* species, *Escherichia coli* O157:H7, *Shigella*)
Glanders (*Burkholderia mallei*)
Melioidosis (*Burkholderia pseudomallei*)
Psittacosis (*Chlamydia psittaci*)
Q fever (*Coxiella burnetii*)
Ricin toxin from *Ricinus communis* (castor beans)
Staphylococcal enterotoxin B
Typhus fever (*Rickettsia prowazekii*)
Viral encephalitis (alphaviruses [e.g., Venezuelan equine encephalitis, Eastern equine encephalitis, Western equine encephalitis])
Water safety threats (e.g., *Vibrio cholerae*, *Cryptosporidium parvum*)

TABLE 2

SECONDARY POTENTIAL BIOLOGICAL THREAT AGENTS

| | |
|---|---|
| Viri/prions | *Histoplasma capsulatum* |
| Flaviviruses (Yellow fever virus, West Nile virus, Dengue, Japanese, Encephalitis TBE, etc.) | *Cryptococcus neoformans* |
| | *Aspergillus niger* |
| | Pathogenic fungi |
| Hepatitis (A, B, C) | *Acremomium* spp. |
| Prions (CJD, BSE, CWD) | *Alternaria alternate* |
| Alphaviruses (VEE, EEE, WEE) | *Apophysomyces elegans* |
| Nipah virus | *Aspergillus terreus* |
| Rabies virus | *Bipolaris* spp. |
| Rhinovirus (could be modified?) | *Bipolaris spicifera* |
| Polioviruses | *Blastoschizomyces capitatus* |
| Hantaviruses | *Candida krusei* |
| Filoviruses (Ebola, Marburg, Lassa) | *Candida lusitaniae* |
| Bacilli | *Cladophialophora bantiana* |
| *Mycobacterium tuberculosis*, drug resistant Mycobacteria other than TB, like *C. leprae* | *Cunnihamella berholletiae* |
| | *Curvularia lunata* |
| | *Exserohilum rostratum* |
| *Streptococcus pneumoniae* | *Fusarium moniliforme* |
| *Streptococcus pyogenes* | *Fusarium solani* |
| *Streptococcus aureus* | *Hansenula anomala* |
| *Clostridium tetani* | *Lasiodilodia theobromae* |
| *Clostridium difficile* | *Malassezia furfur* |
| *Bacillus cereus* | *Paecilomyces lilacinus* |
| *Coxiella brunette* (Q fever) | *Paecilomyces bariotii* |
| *Francisella tularensis* | *Penicillium marneffei* |
| *Borrelia recurrentis* | *Phialemonium curvatum* |
| *Rickettsia rickettsii* | *Phialophora parasitica* |
| *R. prowazekii* | *Phialophora richardsiae* |
| *Shigella sonnei* | *Ramichloridium* spp. |
| *Bartonella henselae* | *Rhizomucor pusillus* |
| *Yersinia enterolitica* | *Rhizopus rhizopodiformus* |
| *Yersinia pseudotuberculosis* | *Rhodotorula rubra* |
| *Neisseria meningitidis* | *Sacchromyces cerevisiae* |
| *Legionella pneumophila* | *Scedosporium prolificans* |
| *Burkholderia pseudomallei* | *Trichosporon beigelii* (*T. asahii*) |
| *Pasturella multocida* | *Wangiella dermatitidis* |
| Other Pathogenic Microorganisms | |
| *Cryptosporidium parvum* | |

TABLE 3

PHYSICAL SIZES OF SOME AGENTS AND SURROGATES

| TARGET | PHYSICAL SIZE |
|---|---|
| *Bacillus thuringiensis* endospore | approximately 1 μm |
| *Bacillus anthracis* endospore | approximately 1 μm |
| *Yersinia pestis* | Gram negative rod-ovoid 0.5-0.8 μm in width and 1-3 μm in length |
| *Yersinia rohdei* | approximately 1 μm |
| Venezuelan Equine Encephalitis | 70 nm (0.07 μm) |
| Gamma-killed MS2 | 2 mD or about 25 nm (0.025 μm) (but will pass through a 300 kD pore size but is retained by a 100 kD pore size Wick and McCubbin - ECBC) |
| Ovalbumin | 45 kD or 6 nm (0.006 μm) |
| Botulinum Toxoid A | 150 to 900 kD or 10 nm to 70 nm (0.01 μm to 0.07 μm)(Normally published as 150 kD however some publications state that toxoid A can be released as complexes comprised of the 150 kD toxin protein along with associated non-toxin proteins and can therefore be released in 900 kD, 500 kD, and 300 kD forms. |
| DNA | 1000 Bp or 600 kD up to 15,000 Bp or 9 mD |

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system for rapid concentration of particles and molecules from a fluid sample, the system comprising:
   a container holding the fluid sample;
   a concentrating pipette tip including a filter, a permeate purge, and a permeate draw, the concentrating pipette tip inserted into the fluid sample container; and
   a concentrating unit adapted to aspirate the fluid sample through the concentrating pipette tip and to collect a concentrated sample from the concentrating pipette tip;
   wherein the fluid sample is aspirated through the concentrating pipette tip, then the concentrated sample is eluted from the filter and dispensed; and
   wherein the filter, the permeate purge, and the permeate draw are connected to a single connection point adapted to couple the concentrating pipette tip to the concentrating unit.

2. The system in claim 1, wherein the permeate purge is in fluid communication with a permeate valve of the concentrating unit.

3. A method for rapid concentration of particles and molecules from a fluid sample, the method comprising:
   connecting a concentrating pipette tip to a concentrating unit, the concentrating pipette tip including a filter, a permeate purge, and a permeate draw, wherein the filter, the permeate purge, and the permeate draw are connected to the concentrating unit via a single connection point, the concentrating unit for aspirating the fluid sample through the concentrating pipette tip, and a permeate valve;
   inserting the concentrating pipette tip into a fluid sample;
   aspirating the fluid sample through the concentrating pipette tip;
   eluting a plurality of particles and molecules in the concentrating pipette tip; and
   extracting a concentrated sample.

4. The method in claim 3, wherein the eluting further comprises backflushing a porous surface within the concentrating pipette tip with a fluid.

5. The method in claim 3, wherein the aspirating further comprises bringing said fluid sample into contact with said porous surface by one or more of air flowing through said porous surface until said fluid sample is aspirated and comes into contact with said porous surface and aspirating air past the porous surface until said fluid sample is aspirated and comes into contact with said porous surface.

6. The method in claim 3, further comprising stopping said fluid sample from flowing past the top of said porous surface so that the fluid sample flows through said porous surface.

7. The method in claim 6, further comprising aspirating a volume of air equivalent to the internal volume of a concentrate side lumen of the porous surface.

8. The method in claim 3, wherein the aspirating further comprises pumping a fluid housed within the concentrating unit past the porous surface and into the fluid sample until a fluid path from the sample to the porous surface is filled with the fluid and said fluid sample can be aspirated and comes into contact with said porous surface.

9. The method in claim 3, wherein the eluting further comprises tangential flushing of a porous surface within the concentrating pipette tip with an elution fluid, wherein the elution fluid is one or more of a liquid elution fluid and a wet foam.

10. The method in claim 3, wherein blinding of the filter is prevented using one or more of high-frequency backpulsing and oscillating tangential flow.

11. The method in claim 3, further comprising pushing fluid onto the filter and pumping the fluid out, wherein the fluid is pushed through one or more of a bore of a hollow fiber filter and a retentate side of a flat filter.

* * * * *